US011103698B2

(12) United States Patent
Chang et al.

(10) Patent No.: US 11,103,698 B2
(45) Date of Patent: Aug. 31, 2021

(54) USING ALTERNATING ELECTRIC FIELDS TO INCREASE CELL MEMBRANE PERMEABILITY

(71) Applicant: Aruna Gambhir

(72) Inventors: Edwin Chang, Menlo Park, CA (US);
Chirag B. Patel, Palo Alto, CA (US);
Sanjiv S. Gambhir, Portola Valley, CA (US); Tali Voloshin-Sela, Kibbutz Gvat (IL); Yaara Porat, Kibbutz Gvat (IL);
Moshe Giladi, Moshav Herut (IL)

(73) Assignees: The Board of Trustees of the Leland Stanford Junior University, Stanford, CA (US); Novocure GmbH, Root (CH)

( * ) Notice: Subject to any disclaimer, the term of this patent is extended or adjusted under 35 U.S.C. 154(b) by 0 days.

(21) Appl. No.: 16/864,773

(22) Filed: May 1, 2020

(65) Prior Publication Data
US 2020/0254242 A1    Aug. 13, 2020

Related U.S. Application Data

(63) Continuation of application No. PCT/US2019/040479, filed on Jul. 3, 2019.
(Continued)

(51) Int. Cl.
*A61N 1/32* (2006.01)
*A61P 35/00* (2006.01)
(Continued)

(52) U.S. Cl.
CPC .......... *A61N 1/327* (2013.01); *A61K 41/0061* (2013.01); *A61N 1/025* (2013.01);
(Continued)

(58) Field of Classification Search
CPC .......... A61B 2018/00613; A61B 18/14; A61B 18/1477; A61B 18/1206; A61B 18/0016;
(Continued)

(56) References Cited

U.S. PATENT DOCUMENTS 4,626,506 A * 12/1986 Arnold ............... G01N 33/5005
435/173.9
6,043,066 A *  3/2000 Mangano ............... C12M 35/02
435/173.1
(Continued)

FOREIGN PATENT DOCUMENTS

CA    2985847 A1   11/2016
WO    2014066655 A2   5/2014
(Continued)

OTHER PUBLICATIONS

Kirson et al. "Disruption of Cancer Cell Replication by Alternating Electric Fields." Cancer Res May 1, 2004 (64) (9) 3288-3295. (Year: 2004).*
(Continued)

*Primary Examiner* — Scott J Medway
(74) *Attorney, Agent, or Firm* — Potomac Law Group, PLLC

(57) ABSTRACT

Certain substances (e.g., large molecules) that ordinarily cannot traverse the cell membrane of cells can be introduced into cells by applying an alternating electric field to the cell for a period of time, wherein the frequency of the alternating electric field is selected so that application of the alternating electric field increases permeability of the cell membrane. Once the permeability of the cell membrane has been increased, the substance is able to cross the cell membrane. This approach is particularly useful in the context of cancer cells (e.g., glioblastoma).

20 Claims, 18 Drawing Sheets

Related U.S. Application Data

(60) Provisional application No. 62/795,136, filed on Jan. 22, 2019, provisional application No. 62/728,255, filed on Sep. 7, 2018, provisional application No. 62/693,811, filed on Jul. 3, 2018.

(51) Int. Cl.
*A61K 41/00* (2020.01)
*A61N 1/02* (2006.01)
*A61N 1/36* (2006.01)

(52) U.S. Cl.
CPC ....... *A61N 1/36002* (2017.08); *A61N 1/3603* (2017.08); *A61P 35/00* (2018.01)

(58) Field of Classification Search
CPC ............... A61B 2018/00875; A61N 1/327; A61N 1/05; A61N 1/36002; A61N 1/3603; A61N 1/025; A61N 1/325; A61N 2/004; A61N 2/02; A61N 1/32; A61N 1/205; A61N 1/36034
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Palti |
| 7,465,566 B2* | 12/2008 | Brighton ............ A61N 1/326 435/173.8 |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,313,908 B2* | 11/2012 | Brighton ............ A61N 1/40 435/6.1 |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,020,605 B2* | 4/2015 | McCluskey ........... A61N 1/327 607/62 |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,616,245 B2 | 4/2017 | Kumar |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2* | 9/2020 | Palti ............ A61B 18/12 |
| 2002/0058933 A1* | 5/2002 | Christopherson ...... A61B 18/14 606/34 |
| 2002/0182591 A1* | 12/2002 | Giaever ............ G01N 33/5005 435/4 |
| 2004/0106917 A1* | 6/2004 | Ormsby ............ A61B 18/1492 606/33 |
| 2004/0147984 A1* | 7/2004 | Altshuler ........... A46B 15/0036 607/88 |
| 2005/0209642 A1* | 9/2005 | Palti ............ A61N 1/326 607/2 |
| 2006/0199992 A1* | 9/2006 | Eisenberg ............ A61N 2/006 600/14 |
| 2007/0141106 A1 | 6/2007 | Bonutti et al. |
| 2007/0239213 A1* | 10/2007 | Palti ............ A61N 1/326 607/3 |
| 2010/0259251 A1* | 10/2010 | Boeve ............ A61B 5/05 324/228 |
| 2011/0137229 A1* | 6/2011 | Palti ............ A61N 1/40 604/20 |
| 2014/0330268 A1* | 11/2014 | Palti ............ A61B 90/37 606/34 |
| 2015/0320481 A1* | 11/2015 | Cosman, Jr. ........... A61B 34/10 606/35 |
| 2017/0120041 A1 | 5/2017 | Wenger et al. |
| 2017/0215939 A1* | 8/2017 | Palti ............ A61B 18/12 |
| 2017/0266438 A1* | 9/2017 | Sano ............ A61B 18/1206 |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117969 A1* | 4/2019 | Schmidt ............ A61N 1/32 |
| 2019/0298982 A1 | 10/2019 | Story et al. |
| 2019/0307781 A1 | 10/2019 | Krex et al. |
| 2019/0308016 A1 | 10/2019 | Wenger et al. |
| 2020/0009376 A1 | 1/2020 | Chang et al. |
| 2020/0009377 A1 | 1/2020 | Chang et al. |
| 2020/0061360 A1* | 2/2020 | Hagemann ........ A61M 37/0092 |

FOREIGN PATENT DOCUMENTS

| | | |
|---|---|---|
| WO | 2015175570 A1 | 11/2015 |
| WO | 2016161201 A2 | 10/2016 |

OTHER PUBLICATIONS

Chang et al., "Tumor treating fields increases membrane permeability in glioblastoma cells," Cell Death Discovery, 4:113, 2018.

Chang et al., "Tumor treating fields increases membrane permeability in glioblastoma cells," Proceedings of the 110th Annual Meeting of the American Association for Cancer Research, Mar. 29-Apr. 3, 2019, Atlanta, Georgia, Abstract nr250.

Kessler et al., "Effects of Tumor Treating Fields (TTFields) on Blood Brain Barrier (BBB) Permeability," Neuro. Onc., vol. 20, Suppl. 6, vi93-vi94, Nov. 2018.

Kessler et al., "Effects of Tumor Treating Fields (TTFields) on blood brain barrier permeability," Neuro. Onc., vol. 20, Suppl. 3, p. 286, Sep. 2018.

Kessler et al., "Effects of tumor treating fields (TTFields) on glioblastoma cells are augmented by mitotic checkpoint inhibition," Cell Death Discovery, 5:12, 2019.

Kessler et al., "Tumor treating fields (TTFields) affect the blood brain barrier (BBB) integrity in vitro and in vivo," Proceedings of the 110th Annual Meeting of the American Association for Cancer Research, Mar. 29-Apr. 3, 2019, Atlanta, Georgia, Abstract nr252.

Brown et al., "Development of an adaptive electroporation system for intratumoral plasmid DNA delivery," Biochemistry, vol. 122, pp. 191-198, Apr. 2018.

International Search Report and Written Opinion issued in application No. PCT/US2019/040479 dated Oct. 22, 2019.

(56) References Cited

OTHER PUBLICATIONS

Chang et al., "Synergistic inhibition of glioma cell proliferation by Withaferin A and tumor treating fields," J. Neurooncol., vol. 134, pp. 259-268, Jul. 2017.

* cited by examiner

Effect of TTFields on sensitivity to Lomustine for U87-MG/GFP-Luc cells

Effect of TTFields on sensitivity to Lomustine for pcGBM2/GFP-Luc cells

Effect of TTFields on sensitivity to Lomustine for GBM39 cells

Effect of TTFields on sensitivity to Temozolomide for GBM39 cells

Effect of TTFields on sensitivity to Irinotecan for GBM39/Luc cells

Effect of TTFields on sensitivity to Doxorubicin for MDA-MB-235 cells

Effect of TTFields on sensitivity to Mannose for U87-MG/eGFP-Luc cells

USING ALTERNATING ELECTRIC FIELDS TO INCREASE CELL MEMBRANE PERMEABILITY

CROSS REFERENCE TO RELATED APPLICATIONS

This Application is a continuation of PCT Application PCT/US2019/040479, filed Jul. 3, 2019, which claims the benefit of U.S. Provisional Applications 62/693,811 (filed Jul. 3, 2018), 62/728,255 (filed Sep. 7, 2018), and 62/795,136 (filed Jan. 22, 2019), each of which is incorporated herein by reference in its entirety.

BACKGROUND

The treatment of glioblastoma (GBM) using alternating electric fields is a novel, validated therapy that has become an additional modality (after surgery chemoradiation and chemotherapy) for anti-cancer treatments. Intermediate frequency alternating electric fields (100-500 kHz) have been studied in detail. Most recently, TTFields has been shown to prolong median survival (by 5 months) of glioblastoma patients on maintenance temozolomide chemotherapy. In the context of treating tumors, alternating electric fields at these frequencies are often referred to as "tumor treating fields" or "TTFields."

Many hypotheses on TTFields' mechanism exist, but the most widely proposed ("standard") mechanism of anti-cancer action by TTFields centers upon the property that tubulin subunits have intrinsic dipole moments. By forcing microtubule structures to align along alternating electric field lines through exogenous imposition of 200 kHz TTFields, the functionality of actively dividing cells is disrupted through interference with the cytoskeleton supporting mitotic spindles. Such stress ultimately promotes impaired cellular proliferation. Proof of concept experiments and relevant technological developments have occurred over the past ten years, culminating in the approval by the Food and Drug Administration (FDA) of a commercial, clinical TTFields device (Optune®, Novocure Ltd.) for the treatment of recurrent and newly-diagnosed glioblastoma.

Over the last few years, additional details about the mechanisms of action have been reported. For instance, TTFields has been shown to disrupt the localization of septins (intracellular proteins responsible for anchoring mitotic spindles during cellular division) and thereby perturb mitosis. Some teams have reported prolongation of DNA damage by chemotherapy or radiotherapy in conjunction with TTFields while others have shown effects on mitochondrial function through the swelling of mitochondrial matrices. Other teams explored combination of chemotherapies (e.g., temozolomide) with TTFields in GBM patients. Such research into combination interventions has uncovered other promising effects against glioblastoma.

SUMMARY OF THE INVENTION

One aspect of the invention is directed to a first method for delivering a substance across a cell membrane of a cell. The first method comprises applying an alternating electric field to the cell for a period of time, wherein application of the alternating electric field increases permeability of the cell membrane; and introducing the substance to a vicinity of the cell, wherein the increased permeability of the cell membrane enables the substance to cross the cell membrane.

In some instances of the first method, the cell is a cancer cell. In some instances of the first method, the cell is a glioblastoma cell. In some instances of the first method, the alternating electric is applied at a frequency of about 200 kHz. In some instances of the first method, the alternating electric field is applied at a frequency between 50 and 190 kHz. In some instances of the first method, the alternating electric field is applied at a frequency between 210 and 400 kHz. In some instances of the first method, the alternating electric field has a field strength of at least 1 V/cm.

In some instances of the first method, the cell is disposed in a body of a living subject, the alternating electric field is applied to the cell by applying an electric field to the subject's body, and the introducing comprises administering the substance to the subject. In these instances, the cell may be a cancer cell. In these instances, the cell may be a glioblastoma cell. In these instances, the alternating electric field may have a frequency between 50 and 190 kHz. In these instances, the alternating electric field may have a frequency between 210 and 400 kHz. In these instances, the alternating electric field may have a field strength of at least 1 V/cm RMS. In these instances, the alternating electric field may have a field strength between 1 and 4 V/cm RMS. In these instances, the step of introducing the substance may begin at a given time, and the step of applying the alternating electric field ends at least 12 hours after the given time. In these instances, the step of applying the alternating electric field may begin at least one hour before the given time. In these instances, the substance may have a molecular weight of at least 1.2 kDa. In these instances, the substance may have a molecular weight of at least 4 kDa. In these instances, the substance may have a molecular weight of at least 20 kDa. In these instances, the substance may have at least one characteristic that ordinarily impedes the substance from crossing the cell membrane. In these instances, the cell may be a cancer cell that is innately resistant to treatment using the substance. In these instances, the cell may comprise a bacterium, and the substance comprises an antibiotic.

Another aspect of the invention is directed to a second method for attacking cancer cells. The second method comprises applying a first alternating electric field at a first frequency to the cancer cells for a first period of time, wherein application of the first alternating electric field at the first frequency to the cancer cells for the first period of time increases permeability of cell membranes of the cancer cells; introducing a substance to the cancer cells, wherein the increased permeability of the cell membranes enables the substance to cross the cell membranes; and applying a second alternating electric field at a second frequency to the cancer cells for a second period of time, wherein the second frequency is different from the first frequency, and wherein the second alternating electric field at the second frequency reduces viability of the cancer cells.

In some instances of the second method, the cancer cells comprise glioblastoma cells, the first frequency is between 250 kHz and 350 kHz, and the second frequency is between 150 kHz and 250 kHz. In some instances of the second method, the cancer cells comprise uterine sarcoma cells, the first frequency is between 125 kHz and 175 kHz, and the second frequency is between 75 kHz and 125 kHz. In some instances of the second method, the cancer cells comprise breast adenocarcinoma cells, the first frequency is between 75 kHz and 175 kHz, and the second frequency is between 100 kHz and 300 kHz. In some instances of the second method, the step of introducing the substance begins at a given time, and the step of applying the first alternating electric field ends at least 12 hours after the given time. In some instances of the second method, the step of applying the first alternating electric field begins at least one hour before the given time. In some instances of the second method, the second period of time comprises a plurality of non-contiguous intervals of time during which the second alternating electric field at the second frequency is applied to the cancer cells, wherein the plurality of non-contiguous intervals of time collectively add up to at least one week.

In some instances of the second method, the cancer cells are disposed in a body of a living subject, the first alternating electric field is applied to the cancer cells by applying a first alternating electric field to the subject's body, the second alternating electric field is applied to the cancer cells by applying a second alternating electric field to the subject's body, and the introducing comprises administering the substance to the subject. In some instances of the second method, the first alternating electric field has a field strength of at least 1 V/cm RMS. In some instances of the second method, the substance has a molecular weight of at least 1.2 kDa. In some instances of the second method, the substance has a molecular weight of at least 4 kDa. In some instances of the second method, the substance has a molecular weight of at least 20 kDa.

Another aspect of the invention is directed to a third method for treating a tumor in a subject's body and delivering a substance across cell membranes in the subject's body. The third method comprises applying a first alternating electric field at a first frequency to the subject's body for a first period of time, wherein application of the first alternating electric field at the first frequency to the subject's body for the first period of time increases permeability of the cell membranes in the subject's body; administering the substance to the subject, wherein the increased permeability of the cell membranes enables the substance to cross the cell membranes; and applying a second alternating electric field at a second frequency to the subject's body for a second period of time that is at least one week long, wherein the second frequency is different from the first frequency, and wherein the second alternating electric field at the second frequency inhibits growth of the tumor.

In some instances of the third method, the tumor comprises a glioblastoma in the subject's brain, the first frequency is between 250 kHz and 350 kHz, and the second frequency is between 150 kHz and 250 kHz. In some instances of the third method, the second period of time comprises a plurality of non-contiguous intervals of time during which the second alternating electric field at the second frequency is applied to the subject's body, wherein the plurality of non-contiguous intervals of time collectively add up to at least one week. In some instances of the third method, the step of administering the substance begins at a given time, and the step of applying the first alternating electric field ends at least 12 hours after the given time. In some instances of the third method, the step of applying the first alternating electric field begins at least one hour before the given time.

In some instances of the third method, the substance has a molecular weight of at least 1.2 kDa. In some instances of the third method, the substance has a molecular weight of at least 4 kDa. In some instances of the third method, the substance has a molecular weight of at least 20 kDa.

Another aspect of the invention is directed to a first apparatus for treating a tumor in a subject's body and facilitating delivery of a substance across cell membranes in the subject's body. The first apparatus comprises an AC voltage generator capable of operating at a first frequency between 50 and 500 kHz and a second frequency between 50 and 500 kHz. Wherein the second frequency is different from the first frequency. The AC voltage generator has a control input, and the AC voltage generator is configured to output the first frequency when the control input is in a first state and to output the second frequency when the control input is in a second state. The first apparatus also comprises a controller programmed to (a) place the control input in the second state so that the AC voltage generator outputs the second frequency, (b) accept a request to switch to the first frequency, (c) upon receipt of the request, place the control input in the first state so that the AC voltage generator outputs the first frequency for an interval of time, and (d) after the interval of time has elapsed, place the control input in the second state so that the AC voltage generator outputs the second frequency.

Some embodiments of the first apparatus further comprise a set of electrodes configured for affixation to the subject's body; and wiring that connects an output of the AC voltage generator to the set of electrodes.

In some embodiments of the first apparatus, the first frequency is between 250 kHz and 350 kHz, and the second frequency is between 150 kHz and 250 kHz. In some embodiments of the first apparatus, the first frequency is between 125 kHz and 175 kHz, and the second frequency is between 75 kHz and 125 kHz. In some embodiments of the first apparatus, the first frequency is between 75 kHz and 175 kHz, and the second frequency is between 100 kHz and 300 kHz. In some embodiments of the first apparatus, the interval of time is at least 12 hours. In some embodiments of the first apparatus, the interval of time is between 12 and 72 hours. In some embodiments of the first apparatus, the controller is further programmed to, subsequent to the receipt of the request, switch the control input back and forth between the first state and the second state.

In some embodiments of the first apparatus, the AC voltage generator is capable of operating at at least one additional frequency between 50 and 500 kHz, and the AC voltage generator is configured to output the least one additional frequency when the control input is in at least one additional state, and the controller is programmed to cycle the control input through the second state and the at least one additional state prior to receipt of the request, and to cycle the control input through the second state and the at least one additional state after the interval of time has elapsed.

Some embodiments of the first apparatus further comprise a user interface, and the request is accepted via the user interface. In some embodiments of the first apparatus, the request is accepted via RF.

BRIEF DESCRIPTION OF THE DRAWINGS

Various embodiments are described in detail below with reference to the accompanying drawings, wherein like reference numerals represent like elements.

DETAILED DESCRIPTION OF THE PREFERRED EMBODIMENTS

As used herein, the term "reducing viability" of a cell refers to reducing the growth, proliferation, or survival of the cell, or increasing cytotoxicity of the cell.

This application describes a novel approach for temporarily increasing the permeability of the plasma cell membranes of cancer cells using alternating electric fields so that substances that are ordinarily blocked by the cell membrane will be able to cross the cell membrane, or so that substances that are ordinarily impeded by the cell membrane will be able to cross the cell membrane more easily. In some of the examples described herein, this approach is used for temporarily increasing the permeability of glioblastoma plasma cell membranes using alternating electric fields so that substances that are ordinarily impeded by the glioblastoma cell membrane will be able to cross the glioblastoma cell membrane more easily.

Figure 1:
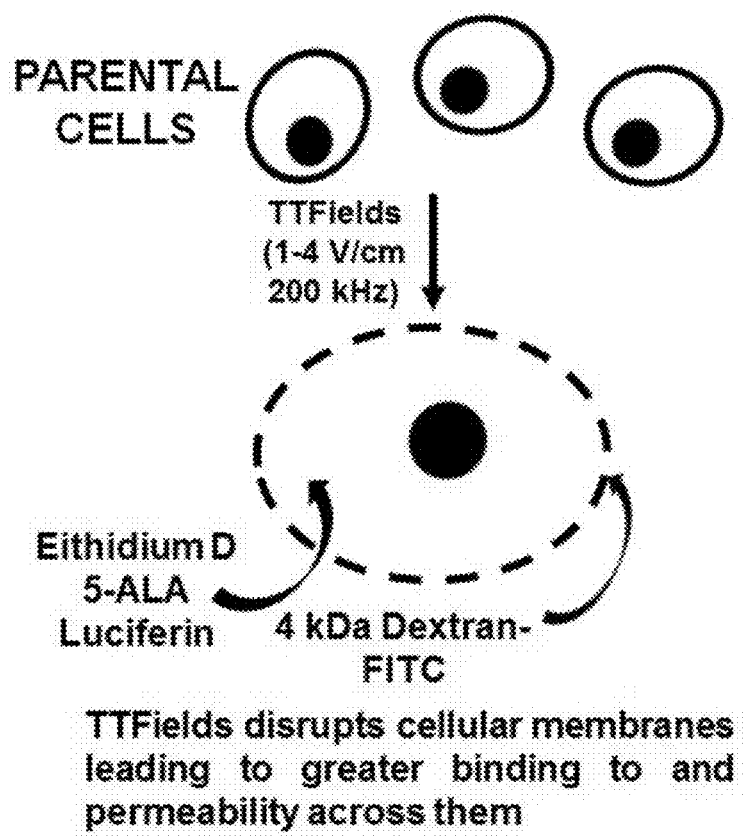
FIG. 1 is a schematic illustration showing an alternative effect of TTFields on modulating the integrity and thus the permeability of cellular membranes.

The inventors have demonstrated that TTFields treatment, in conjunction with a novel anticancer compound Withaferin A, synergistically inhibited the growth of human glioblastoma cells. The inventors hypothesized that such a synergistic effect is due to increased accessibility of Withaferin A to glioblastoma cells through TTFields' capability to increase transiently, tumor cell membrane permeability, as depicted schematically in FIG. 1. In this figure, 5-ALA=5-aminolevulinic acid; Ethidium D=ethidium bromide; and FITC=fluorescein isothiocyanate.

Studies were then performed that validate the hypothesis. In particular, evidence was found to show that TTFields exposure induced greater bioluminescence in human glioblastoma cells that have been modified to express luciferase (renilla and firefly), and that this induction is due to increased permeation of the substrates (D-luciferin and coelenterazine, respectively), through the plasma membrane. Increased membrane permeability caused by TTFields exposure was also demonstrated with other membrane-penetrating reagents such as Dextran-FITC and Ethidium D.

Using TTFields to increase membrane permeability in glioblastoma cells was also shown using 5-aminolevulinic acid (5-ALA). 5-ALA is a hemoglobin precursor that is converted into fluorescent protoporphyrin IX (PpIX) in all mammalian cells. However, many malignant cells, including high-grade gliomas, have elevated hemoglobin biosynthesis, which is reflected in enhanced accumulation of PpIX within transformed cells and tissues (compared to non-cancerous cells). This property has prompted many medical investigations to use 5-ALA uptake (and, by consequence, its enzymatic conversion to PpIX) as a fluorescent biomarker for tumor cells. However, at the current level of technology, it can be difficult to distinguish the precise cellular margin between tumor and non-tumor tissue intraoperatively. Experiments described herein show that TTFields significantly enhances the tumor to normal cell ratio for PpIX fluorescence (brought on by 5-ALA exposure and uptake), and in this manner, may be used to better delineate tumor margins in intraoperative settings.

Further experiments using scanning electron microscopy (SEM) data demonstrate an increase in the number and size of holes in glioblastoma cell membranes caused by TTFields exposure, and that the morphology of the glioblastoma cell membrane is perturbed when TTFields are applied. Through all modalities studied (bioluminescence, fluorescence, and SEM), the effects of TTFields on the GBM cell membrane permeability were found to be reversible after cessation of TTFields exposure.

Results

Induction of TTFields Increases Bioluminescence (BLI) in Luciferase-Expressing Glioblastomas.

Figure 2A:
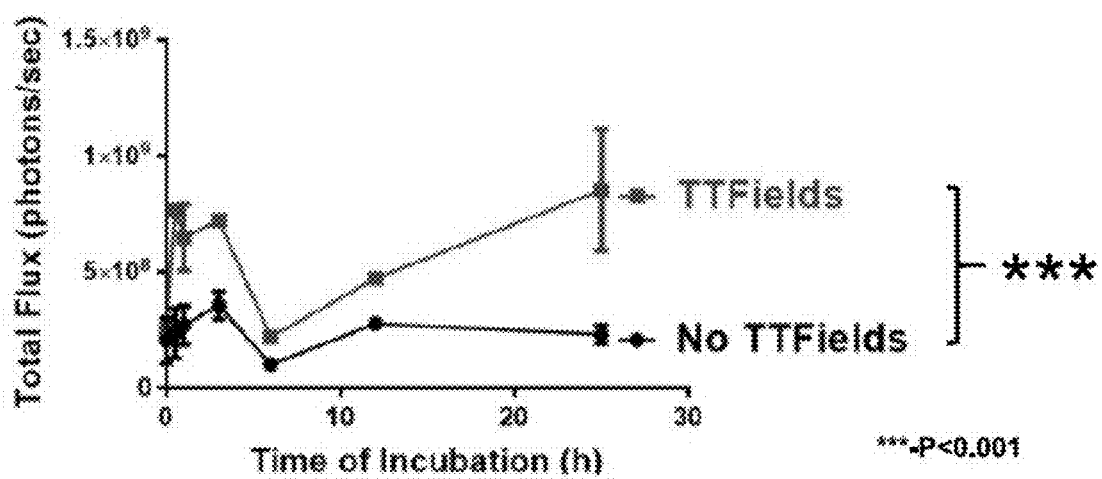
FIG. 2A depicts exemplary effects of TTFields on bioluminescence of U87-MG/eGFP-fLuc cells from bioluminescent imaging scans as a function of time in TTFields vs. no TTFields conditions.

U87-MG/eGFP-fLuc cells were seeded on Thermanox glass coverslips, allowed to settle and grow, and then subjected to either TTFields or no TTFields. In this experiment, the use of TTFields (4 V/cm, 200 kHz, 0.5-24 h duration) significantly increased bioluminescence intensity (BLI) of U87-MG/eGFP-fLuc cells compared to unexposed conditions. This increase in BLI occurred as early as 30 minutes after commencement of TTFields and continued to 24 h of TTFields exposure. When ROI quantification was performed, the time course of BLI intensity for the TTFields-exposed samples was significantly elevated compared to TTFields-unexposed samples ($p<0.0001$, two-way ANOVA, TTFields vs. no TTFields). Data depicting the Temporal quantification of BLI results of these experiments is summarized in FIG. 2A. Without being bound by this theory, it is believed that the elevation in bioluminescence was not due to a direct effect of TTFields on firefly luciferase activity because exposure of purified firefly luciferase to 200 kHz TTFields led to over a 1000-fold loss in enzymatic activity 60 minutes after initiation of TTFields.

Figure 2B:
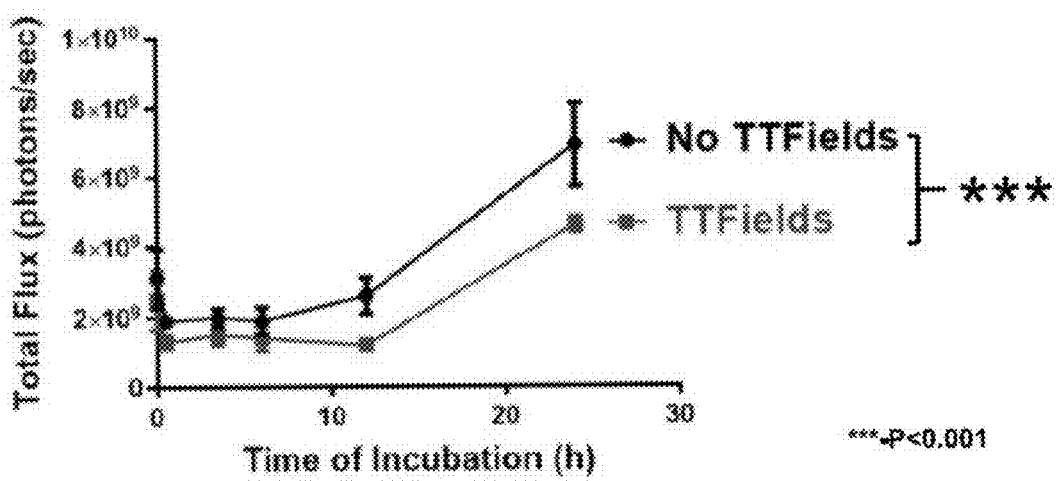
FIG. 2B depicts the exemplary effects of TTFields on eGFP fluorescence for U87-MG/eGFP-fLuc cells as a function of time in TTFields vs. no TTFields conditions.
Figure 2C:
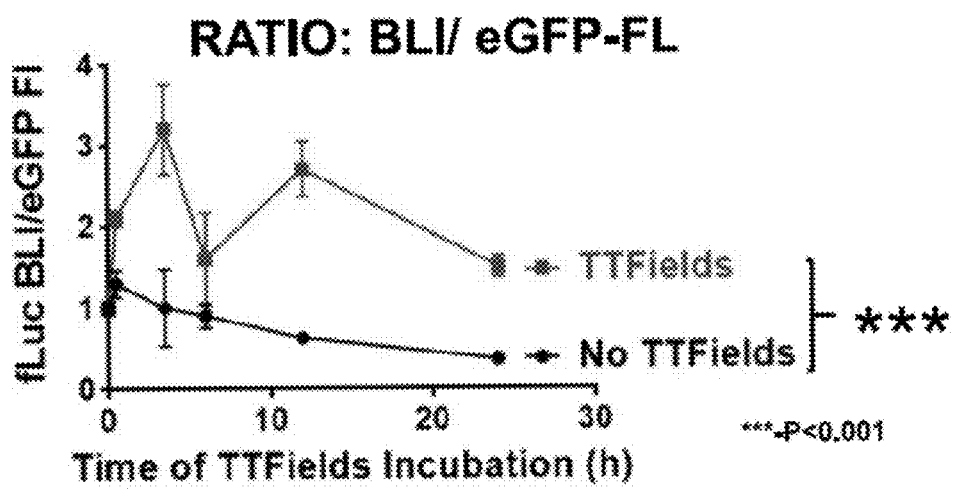
FIG. 2C depicts the effect of TTFields on the fLuc bioluminescence (fLuc-BLI) over eGFP fluorescence (eGFP-FL) ratio for U87-MG/eGFP-fLuc cells as a function of length of TTFields exposure.
Figure 2D:
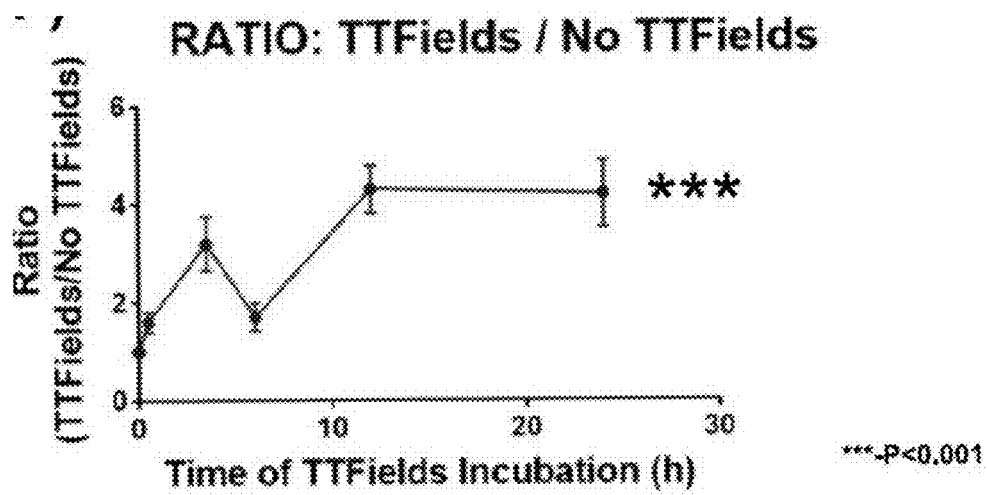
FIG. 2D depicts the effect of TTFields exposure vs. non-exposure on the fLuc-BLI/eGFP-FL ratio as a function of TTFields exposure time.

FIG. 2B depicts the effect of TTFields on eGFP fluorescence in U87-MG/eGFP-fLuc cells observed from time course of representative images (not shown) for TTFields-exposed vs. TTFields-unexposed U87-MG/eGFP-fLuc. The presence of TTFields did not significantly increase eGFP fluorescence (eGFP-FL) over the course of the experiments. When ratios of BLI over eGFP-FL was compared between TTFields vs. no TTFields samples, there was a significantly augmented ratio with respect to time of TTFields incubation for the TTFields samples, as depicted in FIGS. 2C, 2D ($p<0.0001$, two-way ANOVA, TTFields vs. no TTFields). More specifically, FIG. 2C depicts the effect of TTFields on the fLuc bioluminescence (fLuc-BLI) over eGFP fluorescence (eGFP-FL) ratio for U87-MG/eGFP-fLuc cells as a function of length of TTFields exposure; and FIG. 2D depicts the effect of TTFields exposure vs. non-exposure on the fLuc-BLI/eGFP-FL ratio as a function of TTFields exposure time (hours). TTFields significantly decreased activity of purified firefly luciferase compared to no TTFields ($p<0.01$, two-way ANOVA, TTFields vs. no TTFields).

The application of TTFields over time on another patient derived glioblastoma cell line, GBM2/GFP-fLuc also induced a time-dependent increase in bioluminescence in TTFields-exposed GBM2/GFP-fLuc cells when compared to no-TTFields controls ($p<0.0001$, two-way ANOVA, TTFields vs. no TTFields). This same effect was observed in a murine astrocytoma cell line (KR158B) that was genetically modified to express Renilla luciferase-red fluorescent protein fusion protein ($p<0.0001$, two-way ANOVA, TTFields vs. no TTFields). Renilla luciferase activity is not dependent upon ATP and magnesium (as opposed to firefly luciferase). Thus, it is believed that the induction of bioluminescence by TTFields was not due to alterations in endogenous pools of ATP.

Effect of TTFields on Uptake of Membrane-Associating Reagents.

To test if the imposition of TTFields affects cell membrane properties, and thus membrane permeability, the effect of TTFields on the behavior of fluorescently tagged reagents that bind to the cellular membrane was determined. Initially, the impact of TTFields on the binding of Annexin-V-APC to the membrane of U87-MG/eGFP-fLuc cells was measured. Annexin-V-APC binding is a signature of early apoptosis which is characterized by ruffling of the membrane. A positive control for apoptosis (addition of 21 µM Withaferin A to U87-MG/eGFP-fLuc cells) was used to assess the visibility of Annexin-V-APC binding to U87-MG/eGFP-fLuc cells, and showed that such binding could be visualized via fluorescence microscopy over TTFields-unexposed samples. However, when TTFields were applied to U87-MG/eGFP-fLuc cells, Annexin-V-APC binding was not observed at any time point of exposure to TTFields. It therefore appears that TTFields did not induce any significant degree of apoptosis in the U87-MG cells.

Figure 3A:
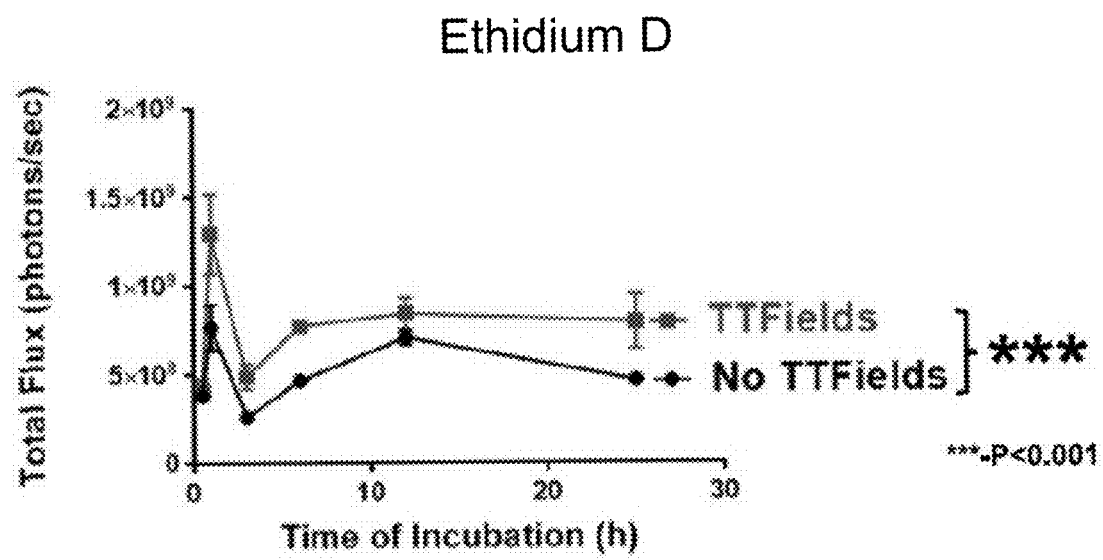
FIG. 3A depicts the exemplary effects of TTFields on time-dependent uptake of Ethidium D in U87-MG/eGFP-fLuc cells between no TTFields and TTFields (200 kHz).

Notably, ethidium D uptake was significantly increased when the U87-MG/eGFP-fLuc cells were subjected to 200 kHz TTFields, as depicted in FIG. 3A ($p<0.0001$, two-way ANOVA, TTFields vs. no TTFields). Ethidium D permeates through both the plasma membrane and the nuclear membrane and intercalates into genomic DNA. Thus, these findings suggest that TTFields can have an effect on the permeability of plasma membranes in U87-MG/eGFP-fLuc cells.

Figure 3B:
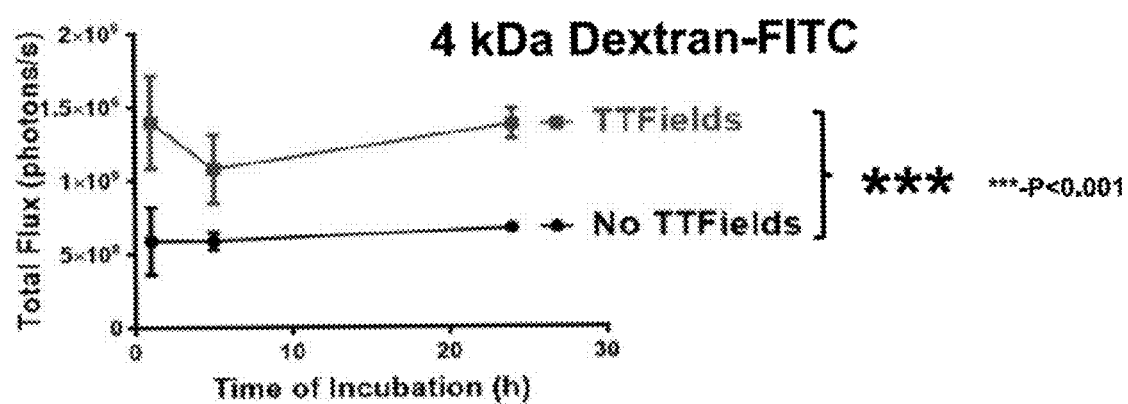
FIGS. 3B-3D depict the exemplary impact of TTFields vs. no TTFields conditions on the time course of Dextran-FITC uptake for 4 kDa Dextran-FITC, 20 kDa Dextran-FITC, and 50 kDa Dextran-FITC, respectively.
Figure 3C:
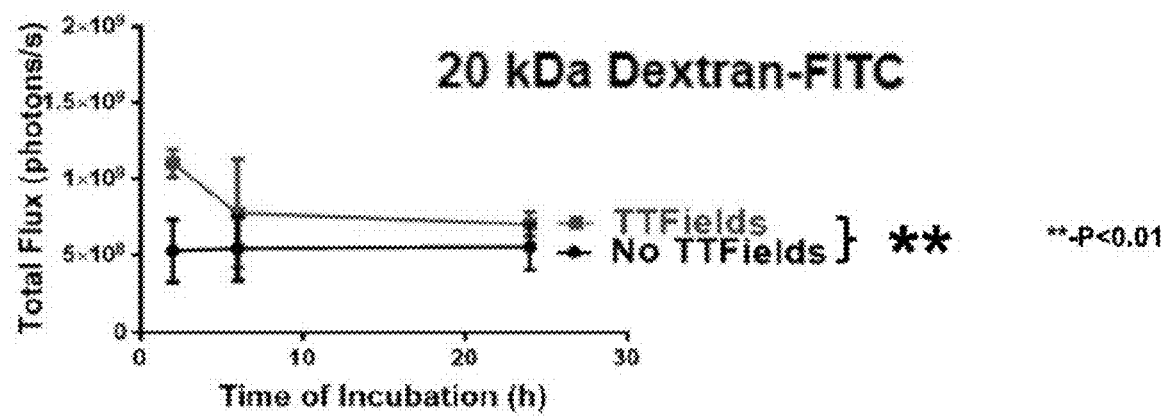
Figure 3D:
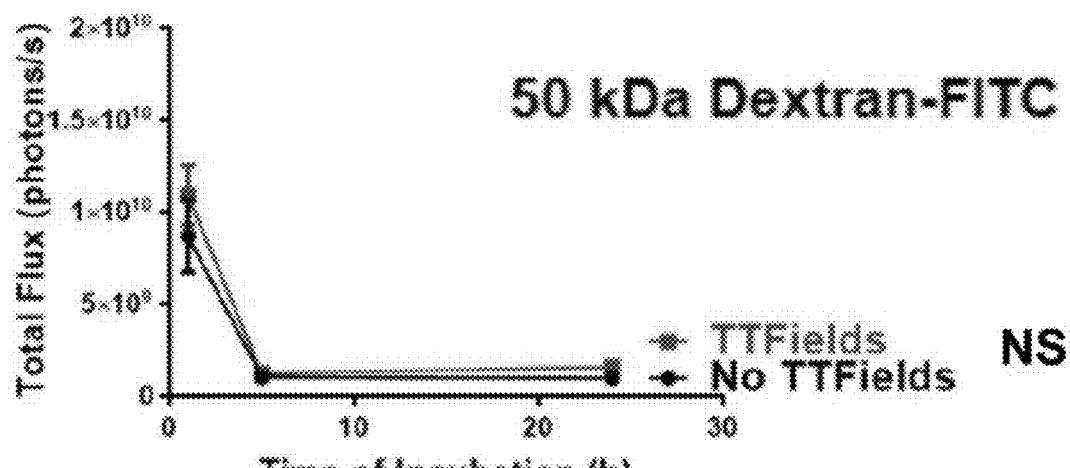

Another consequence of enhanced membrane permeability by TTFields is alterations in Dextran-FITC binding on the cell membrane. Dextran-FITC is known to bind and intercalate into the plasma membrane. When U87-MG cells were subjected to 1 h of 200 kHz TTFields, there was a significant uptake of Dextran-FITC of molecular weights 4 kDa and 20 kDa, compared to no TTFields exposure, as depicted in FIGS. 3B and 3C. But there was no significant difference in uptake for 50 kDa Dextran-FITC, as depicted in FIG. 3D. More specifically, Dextran-FITC binding was examined in the presence of TTFields over a timeframe of 0.5-24 h exposure, a significant increase in the uptake of 4 kDa Dextran-FITC was found compared to TTFields-unexposed samples ($p<0.0001$, two-way ANOVA, TTFields vs. no TTFields), a significant increase in uptake of 20 kDa Dextran-FITC under TTFields exposure ($p<0.01$, TTFields vs. no TTFields) and no significant difference in uptake of 50 kDa Dextran-FITC under TTFields exposure ($p=0.26$, not significant, TTFields vs. no TTFields). These data suggest that the maximum size of Dextran-FITC that bound to and entered the plasma membrane under TTFields exposure in this experiment was between about 20 and 50 kDa. In all statistical comparisons described in this paragraph, each data point represents n=3 experiments. In FIGS. 3A-3D, APC=allophycocyanin; Ethidium D=ethidium bromide; and FITC=fluorescein isothiocyanate.

Effect of TTFields on 5-Aminolevulinic (5-ALA) Acid Uptake: Single U87-MG Culture.

Experiments were performed to determine the effects of TTFields on uptake of 5-ALA (as measured by PpIX accumulation and its resultant fluorescence) in glioblastoma cells. Because it is difficult to distinguish the margin between tumor and normal cells using the present 5-ALA bioassay, the measurement of PpIX fluorescence was used to address this issue. Investigations were run to determine whether permeation of 5-ALA through the cellular membrane and into the glioblastoma cells could be increased with TTFields exposure. U87-MG cells were exposed or unexposed to TTFields, each for durations of 6-24 h. The results, which are summarized in FIG. 4A, were as follows: TTFields exposure resulted in significantly increased uptake of 5-ALA into U87-MG/eGFP-fLuc cells as early as 6 h of TTFields exposure ($p=0.047$, Student's t-test, TTFields vs. no TTFields) and this increase was maintained with prolonged TTFields exposure of 24 h ($p=0.011$).

Figure 4A:
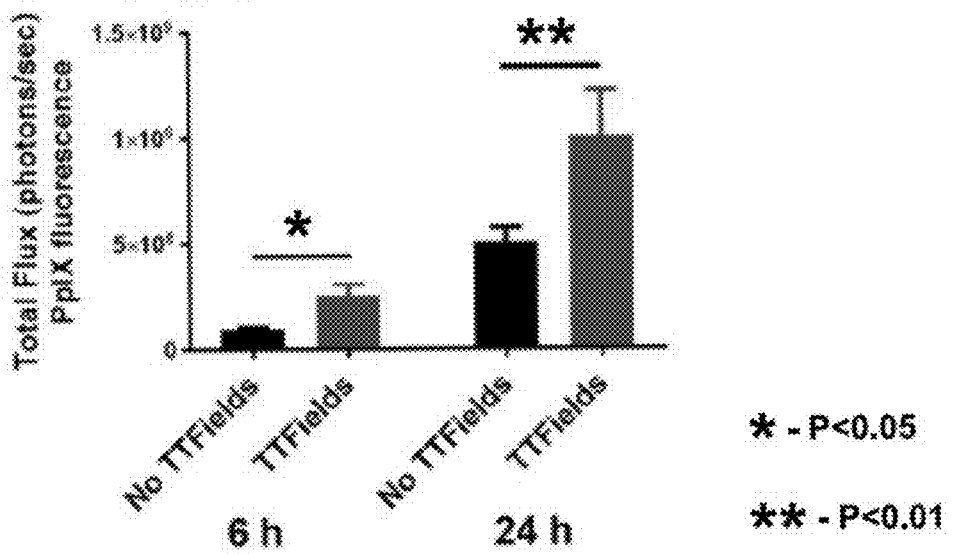
FIG. 4A depicts the exemplary effect of TTFields (200 kHz) on 5-aminolevulinic acid (5-ALA) uptake as shown by representative protoporphyrin IX (PpIX) fluorescence for TTFields vs. no TTFields-exposed U87-MG cells at 6 and 24 hours.

To generate the data depicted in FIG. 4A, protoporphyrin IX (PpIX) fluorescence panels were obtained for TTFields-unexposed vs. TTFields-exposed U87-MG cells after 6 and 24 h of exposure. Quantitation of those images in a showed significant increase in PpIX signals in TTFields exposed cells compared to no TTFields, at both 6 h ($p=0.047$) and 24 h ($p=0.01$) time points. All monovariant statistical comparisons between no TTFields vs. TTFields samples done by Student's t-test for n=3 experiments per time point.

Effect of TTFields on 5-Aminolevulinic Acid Uptake: U87-MG GBM on PCS-201 Fibroblast Co-Cultures.

During glioblastoma resection in patients, 5-ALA is used to aid neurosurgeons in delineating between the tumors and surrounding normal brain tissue. Likewise, to distinguish differences in 5-ALA uptake between glioblastoma and normal cells, a co-culture was developed where U87-MG cells were seeded in the center of a bed of PCS-201 fibroblasts and were subjected to TTFields or to no TTFields. Fluorescent and brightfield photomicrographs confirmed the presence of discrete glioblastoma vs. fibroblast cell regions in the co-culture set-up. When co-cultures were stained with hematoxylin and eosin (H&E), photomicrographs revealed reduced numbers of GBM cells infiltrating into the fibroblast periphery for TTFields-exposed samples.

Figure 4B:
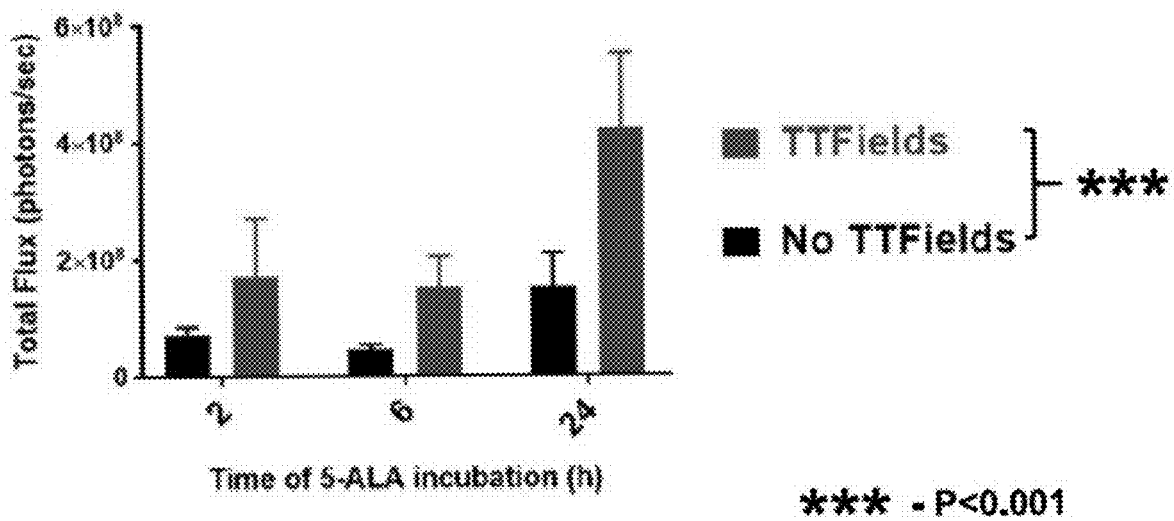
FIG. 4B depicts how PpIX fluorescence changed over time in glioblastoma vs. fibroblast cells in the co-culture platforms that were subjected to TTFields.

In particular, without TTFields exposure, the GBM cells formed many pockets of adherent neurospheres as was previously reported. Fluorescence images showed increased PpIX fluorescence in glioblastoma vs. fibroblast cells in the co-culture platforms that were subjected to TTFields for 6 h. The results, which are summarized in FIG. 4B, were as follows: PpIX fluorescence accumulated over time but the rate of fluorescence intensity increase was significantly augmented ($p<0.001$, two-way ANOVA, TTFields vs. no TTFields) for TTFields-exposed co-cultures compared to TTFields unexposed co-cultures. To generate the data depicted in FIG. 4B, fluorescent panels of 5-ALA uptake (and subsequent PpIX fluorescence, Ex=558 nm, Em=583 nm) for no TTFields and TTFields were obtained. Duration of exposures are 2, 6, and 24 h. Quantification of time course of PpIX accumulation (and thus accumulation of fluorescent flux as expressed as photons/s) in the glioblastoma-fibroblast co-culture platform under TTFields exposed vs. unexposed conditions ($p<0.001$). Statistical analyses consisted of two-way ANOVA for no TTFields vs. TTFields conditions, and n=3 experiments per time point.

In a separate set of experiments, by 24 h of TTFields application, the ratio of PpIX fluorescence intensity in the U87-MG glioblastoma cells over the surrounding PCS-201 fibroblast cells was significantly increased compared to the fluorescence intensity ratio for co-cultured cells under no TTFields conditions ($p=0.043$, two-way ANOVA, TTFields vs. no TTFields).

Scanning Electron Micrograph (SEM) Shows that TTFields Alters Membrane Morphology of U87-MG/eGFP-fLuc Cells.

Figure 5:
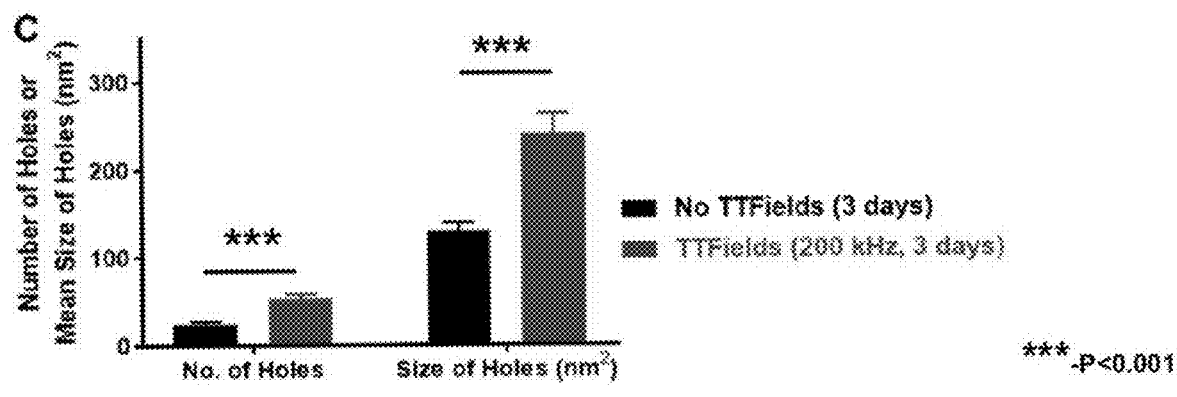
FIG. 5 provides quantification of the number and size of holes from a SEM comparison of plasma membrane holes in U87-MG/eGFP-fLuc cells exposed and unexposed to TTFields for 3 days.

SEM images of low density (5,000 cells/coverslip) U87-MG/eGFP-fLuc cells that were either not exposed to TTFields or exposed to TTFields for 3 days were obtained at 2000×, 20,000×, and 60,000× magnifications. Data obtained by reviewing these SEM images is summarized in FIG. 5. There was a significantly increased number of holes greater than 51.8 $nm^2$ in size (equivalent to 9 $pixels^2$ on 60,000× magnification) within the ROI of TTFields-exposed cells (53.5±19.1) compared to the TTFields-unexposed cells (23.9±11.0), ($p=0.0002$, univariate Mann-Whitney test). Average size of the holes within the ROI was also significantly greater in TTFields-exposed cells (240.6±91.7 $nm^2$) compared to TTFields-unexposed cells (129.8±31.9 $nm^2$), ($p=0.0005$ (univariate Mann-Whitney test)). To obtain the data depicted in FIG. 5, Quantification and comparison between TTFields unexposed and exposed cells of the number and size of holes was done within a 500 nm-radius circular region of interest. The minimum hole size cut-off was based on the 3.3 and 5.0 nm Stokes radii of 20 kDa and 50 kDa Dextran-FITCs, respectively. Coverslips from three experiments per condition were used, and at least 5 cells per coverslip were analyzed for hole count and size, in a double-blind manner.

The effects of a 24-h exposure to TTFields on the plasma membranes of U87-MG cells seeded at high density were also visually observed. For the no TTFields samples, the cell surface appeared to be covered in densely matted, elongated and flattened membrane extensions, similar to membrane ruffles and contiguous with the cellular membrane. In contrast, after 24 h of exposure to TTFields, the densely matted and elongated structures were replaced by short, bulbous and bleb-like structures.

Figure 6:
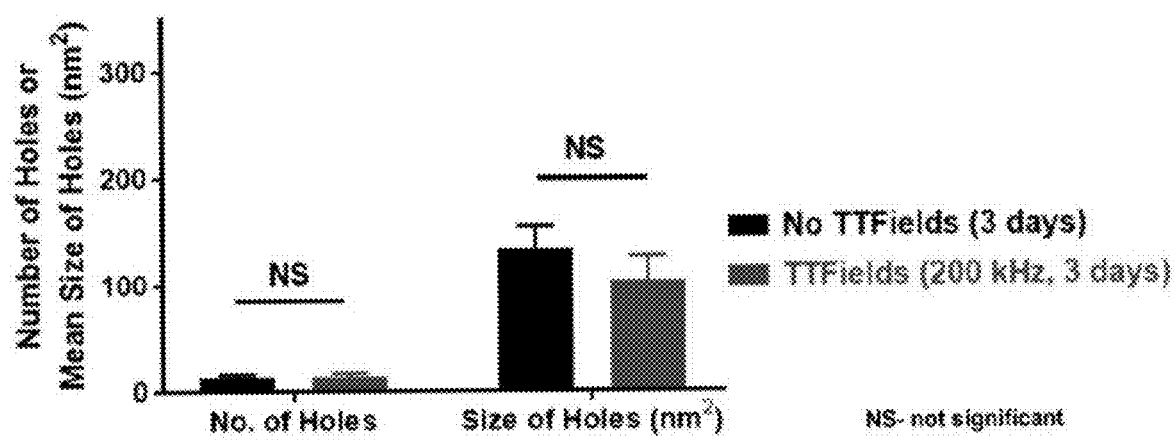
FIG. 6 provides quantification of the number and size of holes from a SEM comparison of plasma membrane holes in normal human PCS-201 cells exposed and unexposed to TTFields for 3 days.

For comparison, SEM images of normal human PCS-201 cells were also obtained and analyzed. PCS-201 cells were seeded at low density (5,000 cells per 13 mm glass coverslip). The cells were grown under standard tissue culture conditions (37° C., 95% 02, 5% $CO_2$). Non-TTFields-exposed cells were left under those conditions for the duration of the study. Other cells were exposed to TTFields for 72 h. After 72 hours, the SEM images were obtained at 2000×, 20,000×, and 60,000× magnifications. Quantification and comparison between TTFields unexposed and exposed cells of the number and size of holes with area ≥51.8 $nm^2$ (equivalent to a 4-nm radius circle, or 9 $pixels^2$ on the 60,000× magnification images) within a 500 nm-radius circular region of interest. The minimum hole size cut-off was based on the 3.3 nm and 5.0 nm Stokes radii of 20 kDa and 50 kDa Dextran-FITCs, respectively. The results, which are depicted in FIG. 6, were as follows: There was no significant difference in the number or size of holes between the TTFields unexposed and exposed normal human PCS-201 cells (Wilcoxon rank-sum analysis). Coverslips from three experiments per condition were used, and at least 5 cells per coverslip were analyzed for hole count and size, in a double-blind manner The effects of a 24-h exposure to TTFields on the plasma membranes of PCS-201 cells were also visually observed. Unlike the situation described above for the U87-MG cells, TTFields did not appear to alter the membrane morphology of the PCS-201 cells.

The Effect of TTFields on Membrane Permeability is Reversible.

Figure 7A:
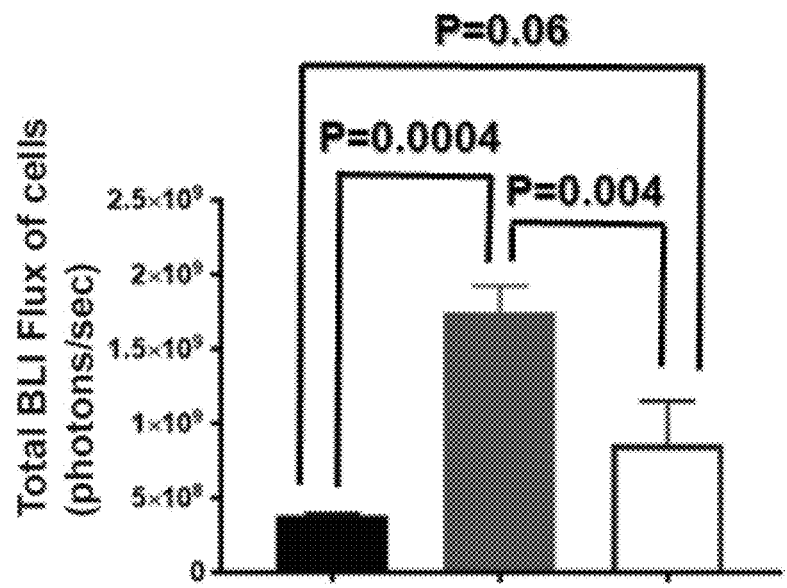
FIG. 7A-7C depict the results of experiments showing how alternating electric fields reversibly increase uptake in U87-MG cells of D-Luciferin, 5-ALA, and Dextran-FITC (4 kDa), respectively.
Figure 7B:
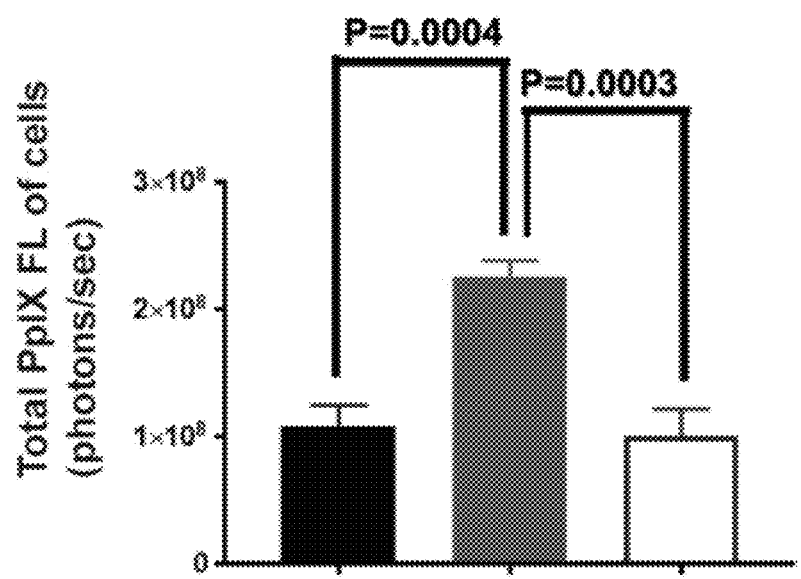
Figure 7C:
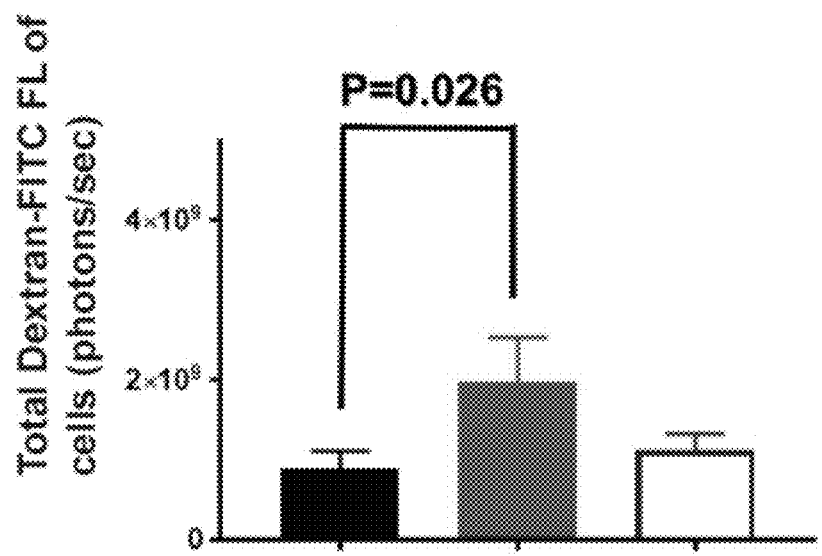

To assess the reversibility of the effect of TTFields on cancer cells, U87-MG/eGFP-fLuc cells were subjected to three conditions: (1) No TTFields exposure, standard cell culture conditions (37° C., 95% 02, 5% $CO_2$), (2) TTFields exposure for 24 h and (3) TTFields exposure for 24 h followed by no TTFields exposure for 24 h. The readouts of BLI, PpIX fluorescence (5-ALA product) and Dextran-FITC (4 kDa) fluorescence were acquired. All experimental conditions were done in triplicate. FIG. 7A summarizes the data for BLI: The presence of TTFields for 24 h (middle bar) significantly increased BLI flux compared to no TTFields exposure (left bar) ($p<0.0005$, two-way ANOVA, TTFields vs. no TTFields) but this increase was significantly attenuated when the cells were re-introduced to the no TTFields condition for 24 h (right bar) (two-way ANOVA, $p<0.005$, TTFields for 24 h vs. TTFields for 24 h followed by no TTFields for 24 h). FIG. 7B shows that a similar pattern of reversible readouts occurred with PpIX fluorescence ($p<0.0005$, two-way ANOVA, TTFields (middle bar) vs. no TTFields (left bar) and $p<0.0004$, TTFields vs. TTFields followed by no TTFields (right bar)). And FIG. 7C shows that a similar pattern of reversible readouts occurred for 4 kDa Dextran-FITC fluorescence ($p<0.05$, two-way ANOVA, TTFields (middle bar) vs. no TTFields (left bar); and $p<0.05$, TTFields vs. TTFields followed by no TTFields (right bar)). For each experimental set, eGFP fluorescence did not significantly change. SEM investigations also revealed that the significant augmentation in both the number of holes ($p=0.007$, two-way ANOVA, TTFields vs. No TTFields) and the size of holes ($p=0.0007$, two-way ANOVA, TTFields vs. No TTFields) by TTFields were reversible as well, after 24 h of no exposure. Here, NS=not significant; BLI=bioluminescent imaging; eGFP=enhanced green fluorescence protein; fLuc=firefly luciferase; 5-ALA=5 aminolevulinic acid; FITC=fluorescein isothiocyanate; PpIX=protoporphyrin IX; and FL=fluorescence.

To summarize, the uptake of the relevant compounds increased when alternating electric fields were applied (as compared to when alternating electric fields were not applied). Each of these figures also shows that the uptake decreased substantially after cessation of the alternating electric fields for 24 hours. From this, we can infer that the increase in permeability of the cell membranes that was induced by the alternating electric fields is not a permanent effect, and that the permeability drops back down after cessation of the alternating electric fields.

Figure 7D:
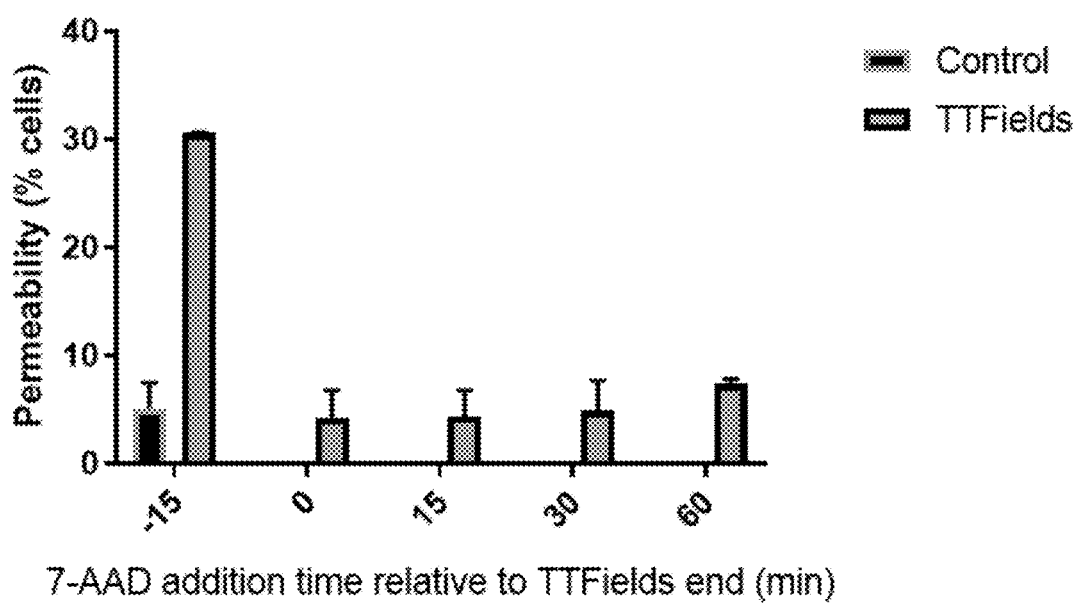
FIG. 7D depicts the results of an experiment that shows timing characteristics of the permeability that is induced by the application of TTFields to U87-MG cells.

FIG. 7D depicts the results of an experiment to test how quickly the permeability drops back down after cessation of the alternating electric fields. More specifically, 7-Aminoactinomycin D (7-AAD) is a fluorescent chemical compound with a strong affinity for DNA. 7-AAD is a relatively large molecule (1270.43 g/mol, i.e., 1.27 kDa) that ordinarily does not readily pass through intact cell membranes. FIG. 7D shows timing characteristics of the permeability to 7-AAD that is induced by the application of TTFields for U87-MG cells. In this experiment, the cells were treated with an alternating electric field at 300 kHz with a field strength of 1.62 V/cm RMS for 24 hours, at an ambient temperature of 18° C. 7-AAD was introduced into samples at five different times: 15 minutes prior to the cessation of the alternating electric field; immediately after cessation of the alternating electric field; and 15, 30, and 60 minutes after cessation of the alternating electric field. In each case, the cells were incubated with 7-AAD for 30 minutes after introduction of the 7-AAD, followed by flow cytometry analysis of the percentage of cells with increased accumulation of the fluorescent 7-AAD for each of the different timings. As seen in FIG. 7D, a significant increase in accumulation of 7-AAD was observed only in the sample that was incubated with 7-AAD while subjected to an alternating electric field.

Additional Results for Different Drugs and Different Types of Cancer Cells.

The methods described herein are not limited to the context of glioblastoma. To the contrary—they are applicable to other types of cancer cells. More specifically, a substance can be delivered across a cell membrane of a cell by (a) applying an alternating electric field to the cell for a period of time, wherein application of the alternating electric field increases permeability of the cell membrane; and (b) introducing the substance to a vicinity of the cell. The increased permeability of the cell membrane enables the substance to cross the cell membrane. Notably, the methods described herein may be used to deliver large molecules (which ordinarily would not pass through the relevant cell membrane) through a cell membrane of different types of cells (i.e., cells other than glioblastoma), including but not limited to other types of cancer cells (e.g., MDA-MB-435 and MCF-7 cells).

Figures 8A, 8B, 8C:
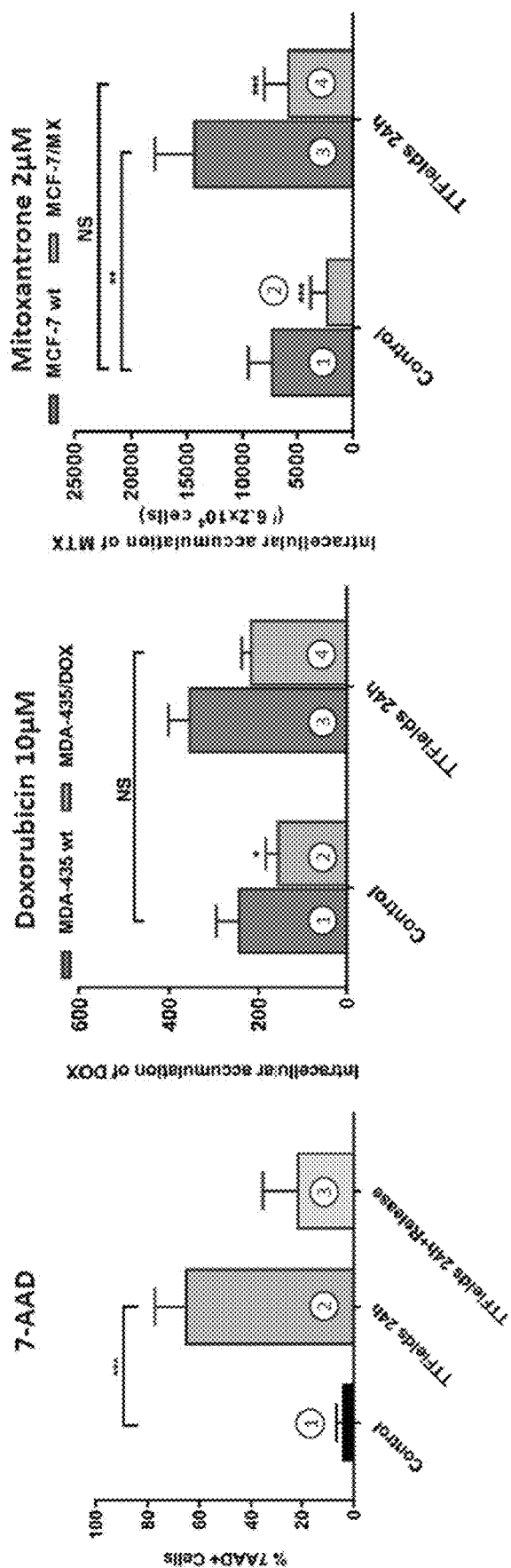
FIG. 8A depicts the results of an experiment showing how alternating electric fields affect the permeability of MDA-MB-435 cell membranes to 7-AAD.
FIG. 8B depicts the results of an experiment showing how alternating electric fields affect the permeability of MDA-MB-435 and MDA-MB-435 Doxycycline resistant cell membranes to doxorubicin.
FIG. 8C depicts the results of an experiment showing how alternating electric fields affect the permeability of MCF-7 and MCF-7 Mitoxantrone resistant cell membranes to mitoxantrone.

FIG. 8A depicts the results of an experiment performed to determine how alternating electric fields affect the permeability of the cell membranes of MDA-MB-435 human melanoma cell line cells. In this experiment, MDA-MB-435 cells were treated with an alternating electric field at 150 kHz with a field strength of 1.62 V/cm for 24 hours, at an ambient temperature of 18° C. and a dish temperature of 37° C. (The dish temperature in this and other examples is higher than the ambient temperature due to heating caused by the alternating electric fields.) After the first 23.75 hours, 7-AAD was added to the culture and incubated for 15 minutes during which time the alternating electric fields was continued (to complete the 24 hour period). After this 15 minute period, alternating electric field application was terminated and the cells were incubated at room temperature for an additional 15 minutes. The percentage of cells with increased accumulation of the fluorescent 7-AAD was determined using flow cytometry analysis. ~66% of the cells exhibited an increased accumulation of 7-AAD (bar 2 in FIG. 8A), as compared to less than 5% of the cells in the control (bar 1), which was subjected to the same conditions, except that the alternating electric fields were not applied. These results indicate that alternating electric fields cause a very significant increase in the permeability of cell membranes.

In a variation of this experiment, MDA-MB-435 human melanoma cell line cells were treated with an alternating electric field at 150 kHz with a field strength of 1.62V/cm for 24 hours, at an ambient temperature of 18° C. and a dish temperature of 37° C. After this 24 hour period, the alternating electric fields were turned off for 15 minutes, after which the 7-AAD was added. After waiting an additional 15 minutes, the percentage of cells with increased accumulation of the fluorescent 7-AAD was determined using flow cytometry. This time, only ~20% of the cells exhibited an increased accumulation of 7-AAD (bar 3 in FIG. 8A). These results indicate that the increase in permeability of cell membranes that is induced by alternating electric fields is relatively short-lived, and that the permeability declines rapidly and dramatically after cessation of the alternating electric fields.

FIG. 8B depicts the results of another experiment performed to determine how alternating electric fields affect the permeability of the cell membranes of MDA-MB-435 human melanoma cell line cells to doxorubicin (543.52 g/mol). In this experiment, both wild type and doxorubicin resistant variants of MDA-MB-435 cells were treated with an alternating electric field at 150 kHz with a field strength of 1.62 V/cm for 23 hours. After this 23 hour period, doxorubicin at a concentration of 10 μM was added and incubated for one hour, during which time the alternating electric fields was continued. The intracellular accumulation of doxorubicin was then measured. The intracellular accumulation of doxorubicin increased for both the wild type cells (compare bar 1 to bar 3) and the doxorubicin resistant cells (compare bar 2 to bar 4).

FIG. 8C depicts the results of a similar experiment using MCF-7 human breast adenocarcinoma cell line cells and mitoxantrone (444.481 g/mol). In this experiment, both wild type and mitoxantrone resistant variants of MCF-7 cells were treated with an alternating electric field at 150 kHz with a field strength of 1.62 V/cm for 23 hours. After this 23 hour period, mitoxantrone at a concentration of 2 μM was added and incubated for one hour, during which time the alternating electric fields was continued. The intracellular accumulation of mitoxantrone was then measured. The intracellular accumulation of mitoxantrone increased for both the wild type cells (compare bar 1 to bar 3) and the mitoxantrone resistant cells (compare bar 2 to bar 4).

The results described above in connection with FIGS. 8B and 8C indicate that the alternating electric fields improve intracellular accumulation of chemotherapy molecules in both wild type and drug-resistant cells, and that alternating electric fields can advantageously restore intra-cellular accumulation of chemotherapeutic chemicals in cancer cells after those cells have developed multi drug resistance to those chemicals.

Figure 9A:
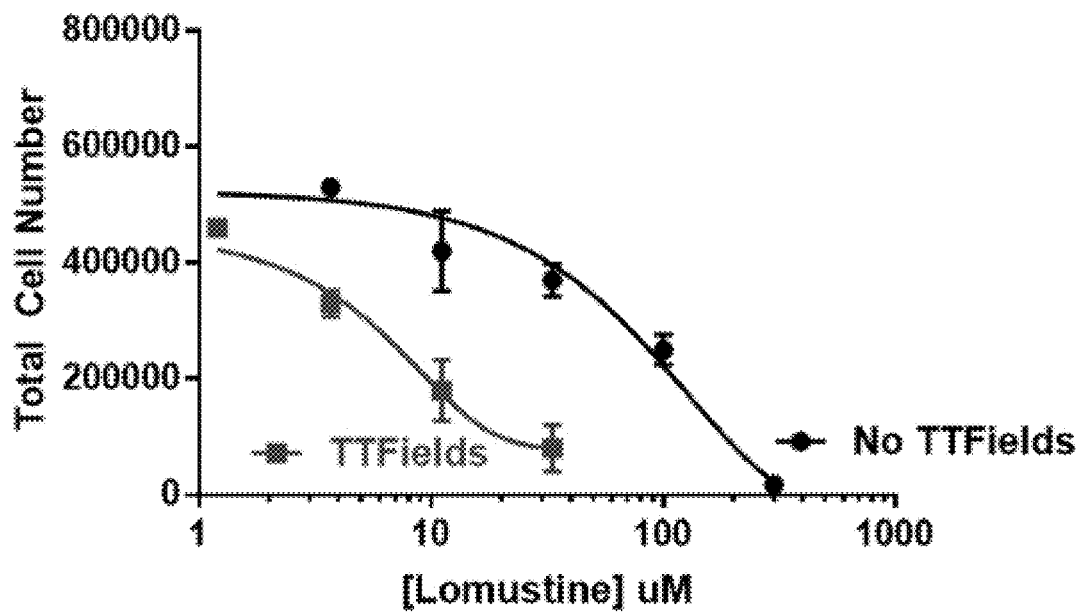
FIGS. 9A-9G depict the effect of TTFields on sensitivity to seven different combinations of substances and corresponding cell types.
Figure 9B:
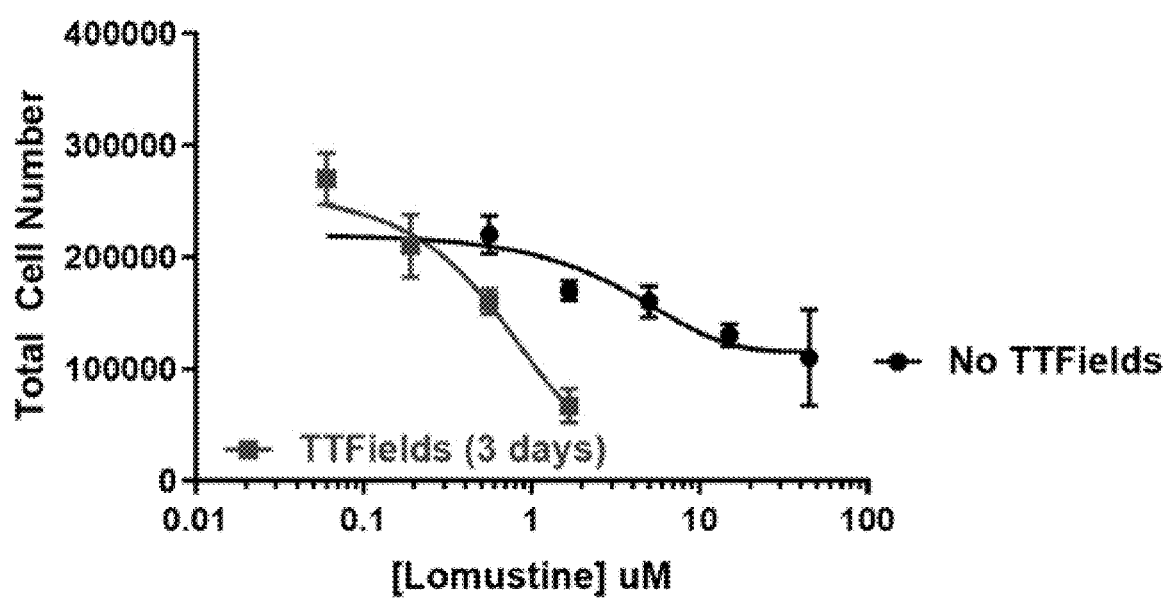
Figure 9C:
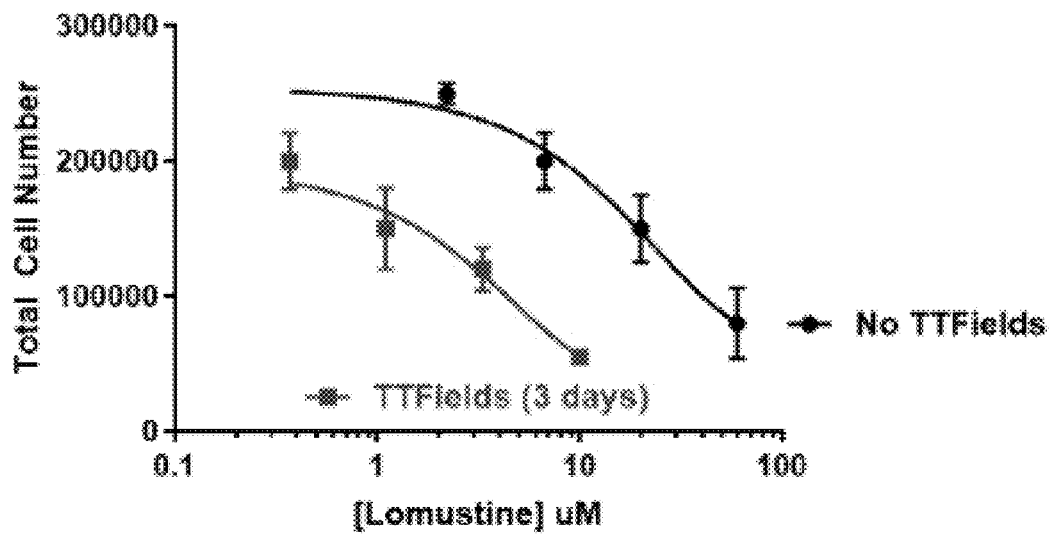
Figure 9D:
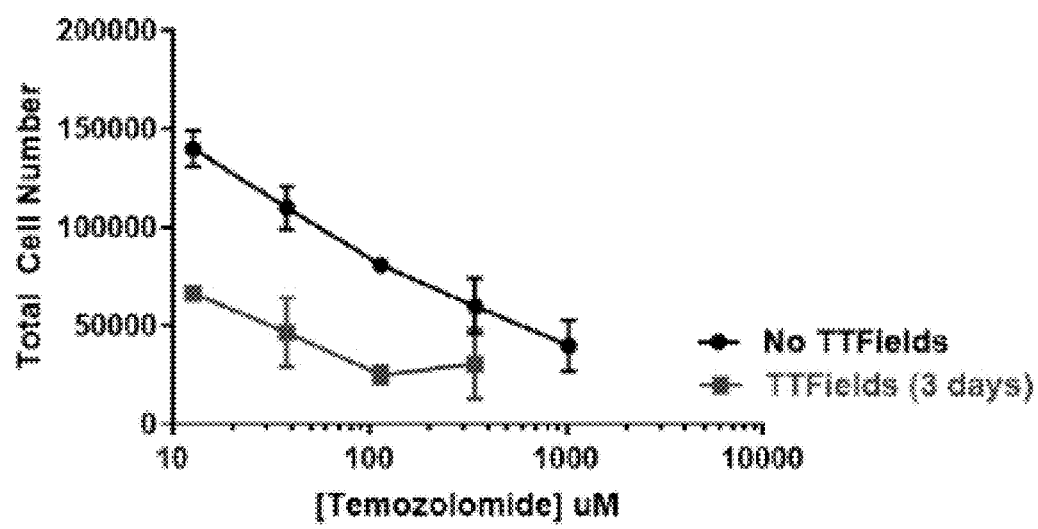
Figure 9E:
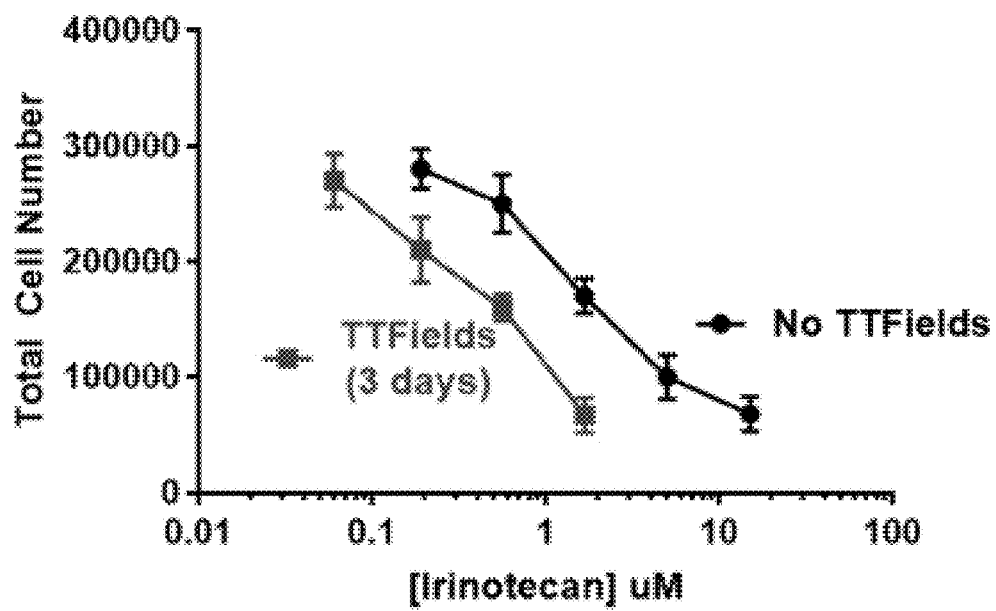
Figure 9F:
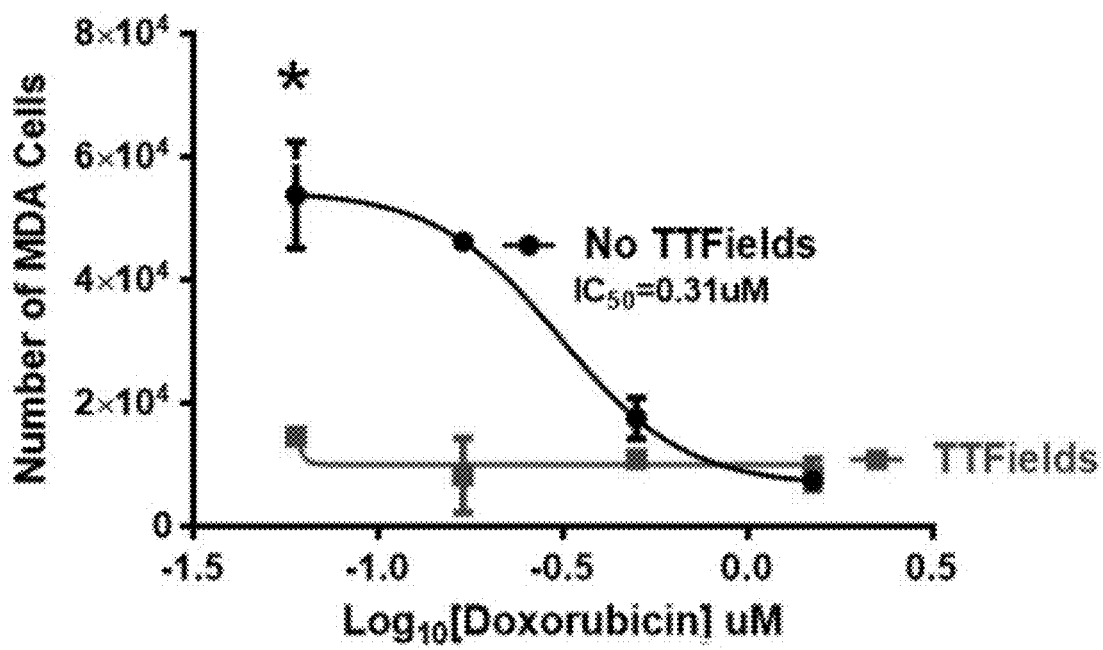
Figure 9G:
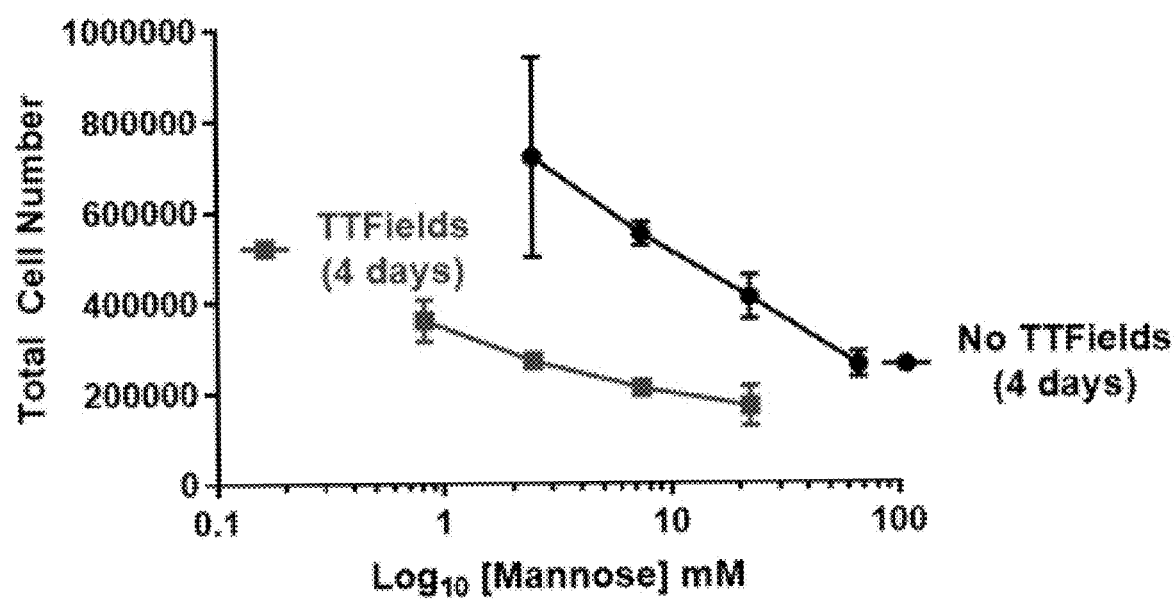

Additional experiments were performed to determine whether synergy exists between TTFields and various drugs for various cancer cell lines, and FIGS. 9A-9G depict the result of some of these experiments. More specifically, FIG. 9A shows how applying TTFields for 3 days improves the sensitivity of U87-MG/GFP-Luc cells to various concentrations of Lomustine (as compared to a control in which TTFields were not applied). FIG. 9B shows how applying TTFields for 3 days improves the sensitivity of pcGBM2/GFP-Luc cells to various concentrations of Lomustine (as compared to a control in which TTFields were not applied). FIG. 9C shows how applying TTFields for 3 days improves the sensitivity of GBM39 cells to various concentrations of Lomustine (as compared to a control in which TTFields were not applied). FIG. 9D shows how applying TTFields for 3 days improves the sensitivity of GBM39 cells to various concentrations of Temozolomide (as compared to a control in which TTFields were not applied). FIG. 9E shows how applying TTFields for 3 days improves the sensitivity of GBM39/Luc cells to various concentrations of Irinotecan (as compared to a control in which TTFields were not applied). FIG. 9F shows how applying TTFields for 3 days improves the sensitivity of MDA-MB-235 cells to various concentrations of Doxorubicin (as compared to a control in which TTFields were not applied). And FIG. 9G shows how applying TTFields for 4 days improves the sensitivity of U87-MG/eGFP-Luc cells to various concentrations of Mannose (as compared to a control in which TTFields were not applied).

To date, synergy was found for the combination of TTFields plus Withaferin A for GBM39/Luc, U87-MG/ GFP-Luc, and pcGBM2/GFP-Luc; synergy was found for the combination of TTFields plus Lomustine for GBM39/ Luc, U87-MG/GFP-Luc, and pcGBM2/GFP-Luc; synergy was found for the combination of TTFields plus Irinotecan for GBM39/Luc; and synergy was found for the combination of TTFields plus Mannose for U87-MG/GFP-Luc. Evidence of synergy was also found for the combination of TTFields plus Doxorubicin for MDA-MB-235.

DISCUSSION

Previous studies have focused on the effects of TTFields on the nucleus (e.g., microtubules), septin, mitochondria, and autophagy. But the experiments described herein are believed to be the first to report the effects of TTFields on cancer cellular membrane integrity, and demonstrate increased cellular membrane permeability for cancer cells (e.g., multiple human GBM cell lines) in the presence of TTFields using various evaluation techniques (e.g., bioluminescence imaging, fluorescence imaging, and scanning electron microscopy).

Observations revealed increased cellular membrane permeability for glioblastomas in the presence of TTFields across multiple human GBM cell lines. The approaches employed to validate the hypothesis included bioluminescence imaging, fluorescence imaging, and scanning electron microscopy. Observations also revealed increased cellular membrane permeability for other types of cancer cells in the presence of TTFields. Studies of TTFields in combination with chemotherapies have shown both therapeutic additivity and synergy. For this study, we posited that TTFields mediates improved accessibility to cancer cells. Several experiments showed the reversibility of the TTFields effect on membranes thus demonstrating a causal relationship between TTFields and the increase in membrane permeability. Such observations also suggest that TTFields could be used to tune drug accessibility to cancer cells.

The investigation into the cell permeability hypothesis of TTFields action was initiated partly because of observations of increased bioluminescence in luciferase-expressing GBM cells by TTFields. While not being bound by this theory, it is believed that TTFields induced increased permeability in the cellular membranes of GBM cells. It is believed that increased GBM cell permeability to D-luciferin as measured by BLI was not due to the effects of TTFields on luciferase itself, but rather due to an increased influx of its substrate D-luciferin into the cells engineered to express the firefly luciferase. Furthermore, this finding held true for both ATP-dependent (FLuc) and ATP-independent luciferase (RLuc). Therefore, despite a preliminary report suggesting that intracellular ATP was increased in CT26 colorectal carcinoma cells exposed to TTFields, the observation of increased glioblastoma cell membrane permeability in the setting of TTFields exposure suggests an independent phenomenon. An increased expression or activation of luciferase due to TTFields exposure could not have explained the increased BLI signal because in these cells the luciferase enzyme was controlled by the same promoter as was eGFP, and an increase in fluorescence signal was not observed in the same cells. However, exposure to TTFields may affect cellular metabolism that would be manifested by changes in ATP levels, alterations in membrane morphology and shifts in oxygen consumption.

Some key findings supporting the permeability hypothesis came from the Dextran-FITC validation experiments described above in connection with FIGS. 3B-D. The accessibility of the cell membrane to small probes in the setting of TTFields was tested with FITC-labeled dextrans, which resulted in an increase in influx of 4 kDa (Stokes' radius ~1.4 nm) and 20 kDa (Stokes' radius ~3.3 nm) but not 50 kDa dextrans (Stokes' radius ~5 nm). This suggests that TTFields cause GBM cells to become more permeant to substances as large as 20 kDa, but no greater than 50 kDa. For reference, the luciferin and coelenterazine substrates are of small enough molecular weight to be accessible through the membrane with TTFields exposure. D-luciferin (substrate for Firefly luciferase) has a molecular weight of 280.3 g/mol (~280 Da), coelenterazine H (substrate for Renilla luciferase) has a molecular weight of 407.5 g/mol (~408 Da), and 5-ALA has a molecular weight of 167.6 g/mol (169 Da), consistent with the Dextran-FITC findings.

The SEM findings described herein reveal that at low seeding density, 3 days of TTFields exposure caused a significant increase in the number and size of holes greater than 51.8 nm$^2$ in area, compared to the no TTFields condition, as described above in connection with FIG. 5. This hole size cut-off represents a circle of radius 4.1 nm, which is the Stokes' radius of a FITC-dextran molecule with a size of 20-40 kDa. Thus, the difference in cell membrane disruption visualized by SEM confirms the indirect observations from the FITC-dextran studies described herein.

Interestingly, exposure of normal human fibroblasts (PCS-201) to TTFields caused no significant increase in the number or size of cellular membrane holes, thus suggesting that the permeability effect may have some specificity to cancer cells. Qualitatively, for U87-MG cells, there was a clear onset of bulbous, bleb-like structures due to a 24-h exposure to TTFields under high seeding density. The appearance of these structures is consistent with increased permeability in the outer membrane and the induction of apoptosis and there appears to be little evidence of an apoptotic phenotype with a 24-h TTFields exposure. Furthermore, high-density PCS-201 cells displayed no such changes with TTFields exposure (data not shown) thus suggesting again, the specificity of the TTFields effect for cancer cells.

Although the cell cycle was not synchronized for the experiments, the doubling time of the U87-MG cells is ~48 h and given that TTFields exert their maximal antiproliferative effect on dividing cells, this could explain the lack of observed abundant apoptosis after a 24-h TTFields exposure. An alternative interpretation may lie in reports that cellular blebbing may confer resistance to cellular lysis. A previous report in unsynchronized glioblastoma cells demonstrated that 72 h of TTFields exposure induced cell death with a marked proportion of Annexin V-positive cells. Using transmission electron microscopy, these reports described signs of autophagy including autophagosomes, swollen mitochondria, and a dilated endoplasmatic reticulum. In contrast, the results herein use SEM to better visualize the effects of TTFields specifically on the plasma cell membrane.

The increase in membrane permeability by TTFields has significant clinical implications. Using the co-culture platform of human GBM cells layered on top of normal human fibroblast cells, the impact of TTFields on the uptake of 5-aminolevulinic acid (5-ALA) into GBM cells was studied. TTFields exposure resulted in significantly increased 5-ALA uptake in the GBM cells compared to the fibroblast cells. In June 2017, 5-ALA was approved by the Food and Drug Administration for clinical use in the United States to assist neurosurgeons in delineating the tumor-normal brain border during glioma resection. Pretreating glioma patients with TTFields prior to 5-ALA administration will therefore be useful to enhance the delineation of the infiltrative tumor margin during tumor resection.

With regard to detecting and measuring the effects of TTFields on cancer cells, the majority of cell culture-based studies to date have focused on cell count/viability as the primary readout. This is based on the prevailing understanding that TTFields interferes with mitosis of rapidly dividing tumor cells, which results in cancer cell death. In addition, computational modeling studies of TTFields in cell culture are currently driven by cell count as the primary outcome of the model.

Recurrence of GBM is inevitable and the median time to first recurrence despite standard therapy is approximately 7 months. In clinical applications of TTFields to patients with GBM, the data suggest that increased compliance and duration of TTFields use correlates with improved survival. TTFields compliance (≥75% vs. <75%) was an independent predictor of overall survival in the retrospective analysis of the full EF-14 trial dataset and the duration of use of TTFields was also found to affect overall survival. Taken together, these data may serve as clinical correlates of the observed effects in the cell cultured-based TTFields experimental setting. Namely, a correlation between the length of TTFields exposure and the duration of its effect on cell membrane permeability after cessation of TTFields was observed. At lengths of TTFields exposure of 0.5-3 h, the duration in BLI augmentation (compared to no TTFields conditions) lasted about 5 min. However, at TTFields exposures of 12-25 h, this difference in BLI between TTFields and no TTFields conditions lasted for more than 20 min. Likewise, a re-analysis of the data reported by Ram et al. shows that the percent increase in overall survival (in patients treated with TTFields plus temozolomide vs. temozolomide alone) jumped from 32% after 1 year of TTFields exposure to 551% after 5 years of TTFields exposure, respectively.

The results described herein i.e., that alternating electric fields increase cellular membrane permeability, are distinct from the previously reported effects of TTFields. This should have a significant impact on current surgical and clinical practices in the treatment of glioblastomas as well as other types of cancer.

In the in vitro experiments described above, the frequency of the alternating electric fields was 200 kHz. But in alternative embodiments, the frequency of the alternating electric fields could be another frequency, e.g., about 200 kHz, between 50 and 500 kHz, between 25 kHz and 1 MHz, between 50 and 190 kHz, between 25 and 190 kHz, or between 210 and 400 kHz.

In the in vitro experiments described above, the field strength of the alternating electric fields was between 1 and 4 V/cm RMS. But in alternative embodiments, different field strengths may be used (e.g., between 0.1 and 10 V/cm).

In the in vitro experiments described above, the alternating electric fields were applied for a variety of different intervals ranging from 0.5 hours to 72 hours. But in alternative embodiments, a different duration may be used (e.g., between 0.5 hours and 14 days). In some embodiments, application of the alternating electric fields may be repeated periodically. For example, the alternating electric fields may be applied every day for a two hour duration.

In the in vitro experiments using the Inovitro™ system described herein, the direction of the alternating electric fields was switched at one second intervals between two perpendicular directions. But in alternative embodiments, the direction of the alternating electric fields can be switched at a faster rate (e.g., at intervals between 1 and 1000 ms) or at a slower rate (e.g., at intervals between 1 and 100 seconds).

In the in vitro experiments using the Inovitro™ system described herein, the direction of the alternating electric fields was switched between two perpendicular directions by applying an AC voltage to two pairs of electrodes that are disposed 90° apart from each other in 2D space in an alternating sequence. But in alternative embodiments the direction of the alternating electric fields may be switched between two directions that are not perpendicular by repositioning the pairs of electrodes, or between three or more directions (assuming that additional pairs of electrodes are provided). For example, the direction of the alternating electric fields may be switched between three directions, each of which is determined by the placement of its own pair of electrodes. Optionally, these three pairs of electrodes may be positioned so that the resulting fields are disposed 90° apart from each other in 3D space. In other alternative embodiments, the electrodes need not be arranged in pairs. See, for example, the electrode positioning described in U.S. Pat. No. 7,565,205, which is incorporated herein by reference. In other alternative embodiments, the direction of the field remains constant.

In the in vitro experiments using the Inovitro™ system described herein, the electrical field was capacitively coupled into the culture because the Inovitro™ system uses conductive electrodes disposed on the outer surface of the dish sidewalls, and the ceramic material of the sidewalls acts as a dielectric. But in alternative embodiments, the electric field could be applied directly to the cells without capacitive coupling (e.g., by modifying the Inovitro™ system configuration so that the conductive electrodes are disposed on the sidewall's inner surface instead of on the sidewall's outer surface).

The methods described herein can also be applied in the in vivo context by applying the alternating electric fields to a target region of a live subject's body, for both glioblastoma cells and other types of cancer cells. Imposing the electric field in the target region will increase the permeability of the cell membranes in the target region, which will enable molecules that are ordinarily blocked or impeded by the cell membrane to pass through the cell membrane. This may be accomplished, for example, by positioning electrodes on or below the subject's skin so that application of an AC voltage between selected subsets of those electrodes will impose the alternating electric fields in the target region of the subject's body.

For example, in situations where the relevant cells are located in the subject's lungs, one pair of electrodes could be positioned on the front and back of the subject's thorax, and a second pair of electrodes could be positioned on the right and left sides of the subject's thorax. In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body. In another embodiment, electrodes could be inserted subcutaneously below a patent's skin. An AC voltage generator applies an AC voltage at a selected frequency (e.g., between 100 and 200 kHz) between the right and left electrodes for a first period of time (e.g. 1 second), which induces alternating electric fields where the most significant components of the field lines are parallel to the transverse axis of the subject's body. Then, the AC voltage generator applies an AC voltage at the same frequency (or a different frequency) between the front and back electrodes for a second period of time (e.g. 1 second), which induces alternating electric fields where the most significant components of the field lines are parallel to the sagittal axis of the subject's body. This two step sequence is then repeated for the duration of the treatment. Optionally, thermal sensors may be included at the electrodes, and the AC voltage generator can be configured to decrease the amplitude of the AC voltages that are applied to the electrodes if the sensed temperature at the electrodes gets too high. In some embodiments, one or more additional pairs of electrodes may be added and included in the sequence. In alternative embodiments, only a single pair of electrodes is used, in which case the direction of the field lines is not switched. Note that any of the parameters for this in vivo embodiment (e.g., frequency, field strength, duration, direction-switching rate, and the placement of the electrodes) may be varied as described above in connection with the in the vitro embodiments. But care must be taken in the in vivo context to ensure that the electric field remains safe for the subject at all times.

A wide variety of applications for increasing the permeability of cell membranes can be readily envisioned in the in vivo context. In one example, localized enhancement of drug uptake by tumor cells can be induced by applying alternating electric fields to the relevant body part for a period of time (e.g., 12 or 24 hours) prior to and during administration of chemotherapies or other antineoplastic agents. In another example, drug uptake by multi drug resistant tumor cells can be restored by applying alternating electric fields to the relevant body part for a period of time (e.g., 12 or 24 hours) prior to and during administration of chemotherapies or other antineoplastic agents. In another example, development of multi drug resistant metastases can be prevented by applying alternating electric fields to regions that are prone to metastases for a period of time (e.g., 12 or 24 hours) prior to and during administration of an appropriate drug (regardless to whether the subject has a primary tumor that is being treated with alternating electric fields).

Figure 10A:
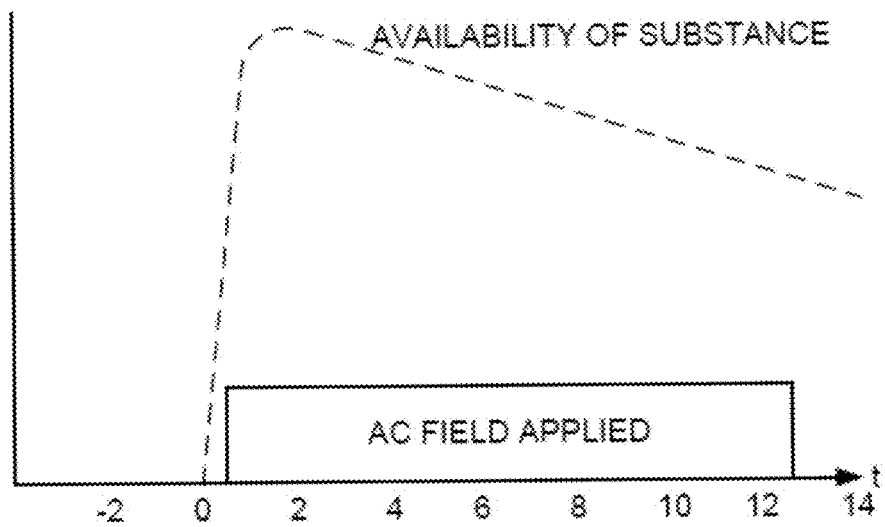
FIGS. 10A and 10B each depict a suitable timing relationship between the application of the alternating electric field and the introduction of the substance to the vicinity of the cancer cell.

FIG. 10A depicts a first suitable relationship in timing between the application of the alternating electric field and the introduction of the substance to the vicinity of the cancer cell in the in vitro context; or between the application of the alternating electric field and the administration of the substance to a live patient. Based on the data described above in connection with FIGS. 7A-7D and 8A, and assuming that the substance is introduced or administered at a given time $t=0$, the alternating electric field can begin after the given time and continue for an interval of time (e.g., 12 hours) while the substance is still available in the vicinity of the cell. In this situation, permeability will begin to increase after the alternating electric field begins, and this increase in permeability will enable the substance to enter the relevant cells. In the context of chemotherapy, this would correspond to administering a chemotherapeutic agent to a patient, followed by application of the alternating electric fields for an interval of time (e.g., for 12 hours).

Figure 10B:
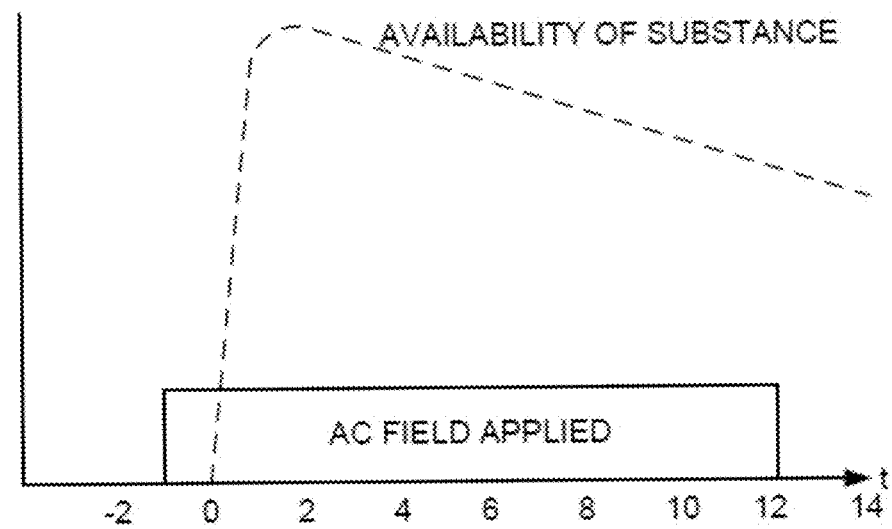

Alternatively, as depicted in FIG. 10B, the alternating electric field can begin before the given time (e.g., 1 hour before $t=0$), and continue for an interval of time (e.g., until 12 hours following $t=0$) while the substance is still available in the vicinity of the cell. In this situation, the permeability of the relevant cells will begin to increase before the substance arrives in the vicinity of the cell (or before the substance is administered to a live patient). This will enable the substance to cross the cell membrane immediately upon its arrival in the vicinity of the cell. In the context of chemotherapy, this would correspond to starting application of the alternating electric fields, followed by the administration of the chemotherapeutic agent while the alternating electric fields are still being applied, followed by continued application of the alternating electric fields for an additional interval of time (e.g., until 12 hours following the time at which the chemotherapeutic agent was administered).

Note that the intervals of time discussed above in connection with FIGS. 10A and 10B can either be uninterrupted or can include breaks that are preferably short. For example, assuming that the interval of time is 12 hours, it could be satisfied by a single uninterrupted block of 12 hours. Alternatively, the 12 hour interval could be satisfied by applying the alternating electric fields for 6 hours, followed by a 1 hour break, followed by applying the alternating electric fields for an additional 6 hours (while the substance is still available in the vicinity of the cell). Note also that in the context of FIGS. 10A and 10B, when the substance is administered to a live patient, the administration of the substance may be performed using any of a variety of approaches including but not limited to intravenously, orally, subcutaneously, intrathecal, intraventricularly, and intraperitonealy.

The optimal frequency, field strength, and switching characteristics may be determined experimentally for each combination of a given type of host cell and a given type of substance that is to be delivered through the cell membrane. In some preferred embodiments, the frequency is less than 190 kHz (e.g., between 50 and 190 kHz or between 25 and 190 kHz. In other preferred embodiments, the frequency is between 210 and 400 kHz.

One existing approach to treating tumors (e.g., glioblastoma) is by applying alternating electric fields at frequencies between 50 and 500 kHz, preferably between 100 and 300 kHz to the tumor. For glioblastoma, 200 kHz is the most preferred frequency. Alternating electric fields at these frequencies are referred to as TTFields, and are described in U.S. Pat. Nos. 6,868,289 and 7,565,205, each of which is incorporated herein by reference in its entirety. Briefly, those two applications describe disrupting dividing cells during mitosis. The effectiveness of TTFields is improved when the direction of the electric field is periodically switched, when the strength of the field in at least a portion of the tumor is at least 1 V/cm, and when the fields are applied for long periods of time (e.g., weeks or months) with as few breaks as possible.

Situations may arise where it will be desirable to treat the tumor with TTFields and also deliver a substance across the cell membranes of the tumor cells (e.g., to help get a therapeutically effective amount of a chemotherapy drug past the cell membranes to provide an additional line of attack against the tumor). In some situations, it may be possible to use a single frequency of an alternating electric field to both treat the tumor and increase the permeability of the cell membranes. In other situations, it may be desirable to use alternating electric fields with different frequencies: a first frequency that is selected to provide improved results for increasing the permeability of the cell membranes, and a second frequency that is selected to provide improved results for the anti-tumor action of the TTFields.

Figures 11A, 11B:
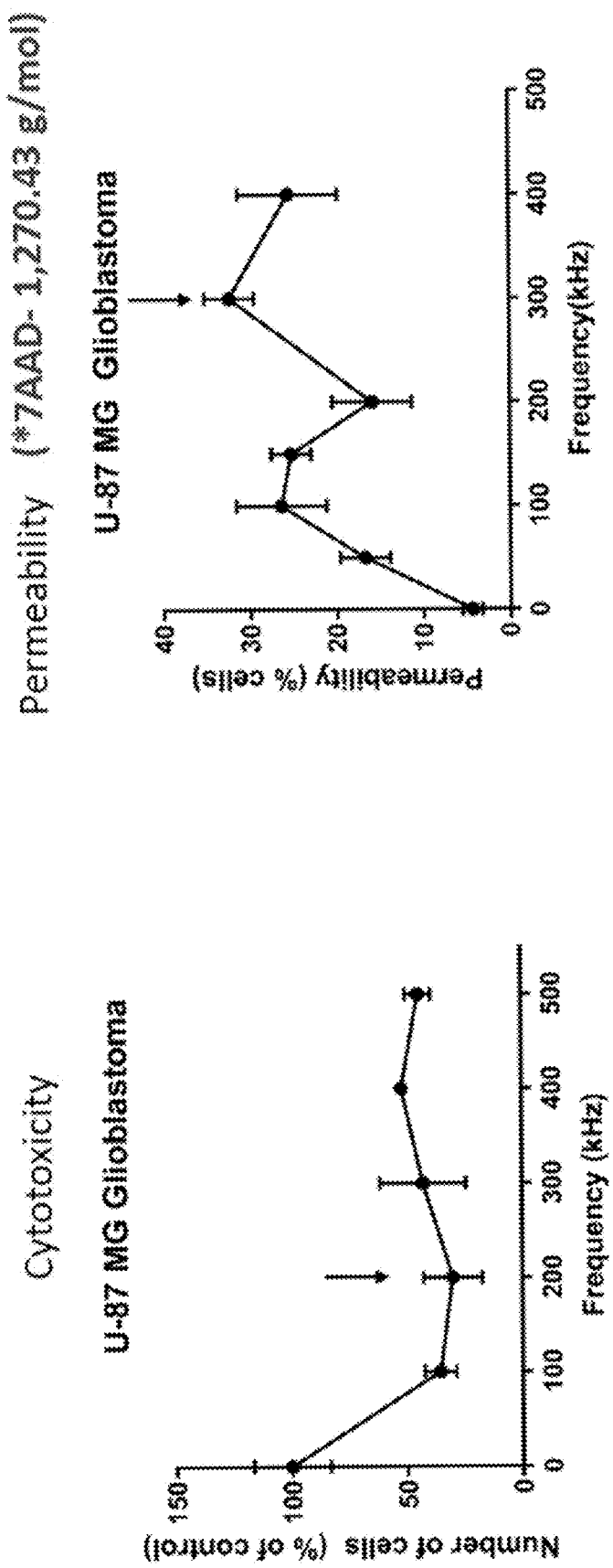
FIG. 11A depicts the results of an experiment to determine the frequency that provides the highest level of cytotoxicity to U-87 MG cells.
FIG. 11B depicts the results of an experiment to determine the frequency that provides the largest increase in permeability of the cell membranes of U-87 MG cells.

FIGS. 11A and 11B depict the results of two in vitro experiments on U-87 MG glioblastoma cells. More specifically, FIG. 11A depicts the results of a first experiment to determine the frequency that provides the highest level of cytotoxicity to U-87 MG cells; and FIG. 11B depicts the results of a second experiment to determine the frequency that provides the largest increase in permeability of the cell membranes of U-87 MG cells.

In the first experiment, the U-87 MG cells were subjected to alternating electric fields with a field strength of 1.62 V/cm RMS at different frequencies for a period of 72 hours at an ambient temperature of 18° C. After this 72 hour period, the number of cells that were present in the sample for each of the different frequencies was measured using flow cytometry. As seen in FIG. 11A, the lowest number of cells (which indicates the highest level of cytotoxicity) was observed for the sample that was subjected to alternating electric fields at 200 kHz.

In the second experiment, permeability to 7-AAD (a fluorescent chemical with a molecular weight of 1270.43 g/mol that ordinarily does not readily pass through intact cell membranes) was measured. In this experiment, the cells were treated with an alternating electric field at different frequencies with a field strength of 1.62 V/cm RMS for a total of 24 hours, at an ambient temperature of 18° C. and a dish temperature of 37° C. After the first 23.75 hours, 7-AAD was added to the culture and incubated for 15 minutes during which time the alternating electric fields was continued (to complete the 24 hour period). After this 15 minute period, alternating electric field application was terminated and the cells were incubated at room temperature for an additional 15 minutes, followed by flow cytometry analysis of the percentage of cells with increased accumulation of the fluorescent 7-AAD for each of the different frequencies. As seen in FIG. 11B, the highest percentage of cells with increased accumulation of 7-AAD (which indicates the highest level of permeability) was observed for the sample that was subjected to an alternating electric field at 300 kHz.

Figure 12B:
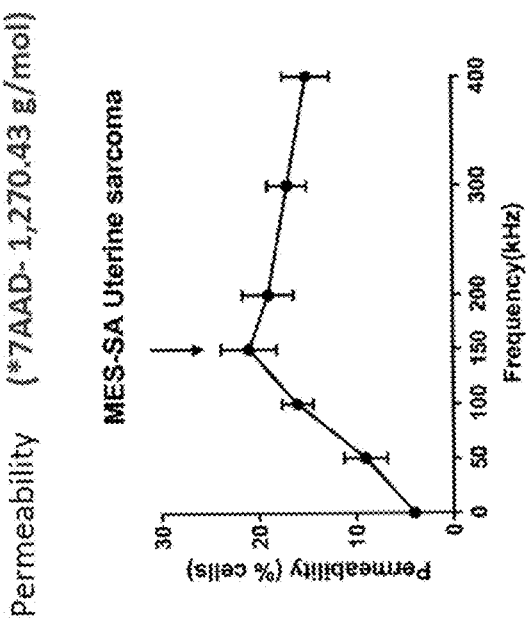
FIG. 12B depicts the results of an experiment to determine the frequency that provides the largest increase in permeability of the cell membranes of MES-SA cells.
Figure 12A:
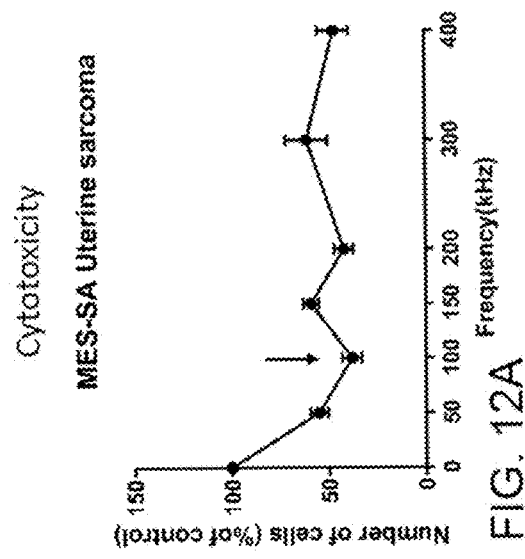
FIG. 12A depicts the results of an experiment to determine the frequency that provides the highest level of cytotoxicity to MES-SA cells.

FIGS. 12A and 12B depict the results of two in vitro experiments similar to those described above in connection with FIG. 11A/B, except that MES-SA uterine sarcoma cells were used. More specifically, FIG. 12A depicts the results of an experiment to determine the frequency that provides the highest level of cytotoxicity to MES-SA cells. The lowest number of MES-SA cells (which indicates the highest level of cytotoxicity) was observed for the sample that was subjected to alternating electric fields at 100 kHz. FIG. 12B depicts the results of an experiment to determine the frequency that provides the largest increase in permeability of the cell membranes of MES-SA cells. The highest percentage of MES-SA cells with increased accumulation of 7-AAD (which indicates the highest level of permeability) was observed for the sample that was subjected to an alternating electric field at 150 kHz.

Figure 12C:
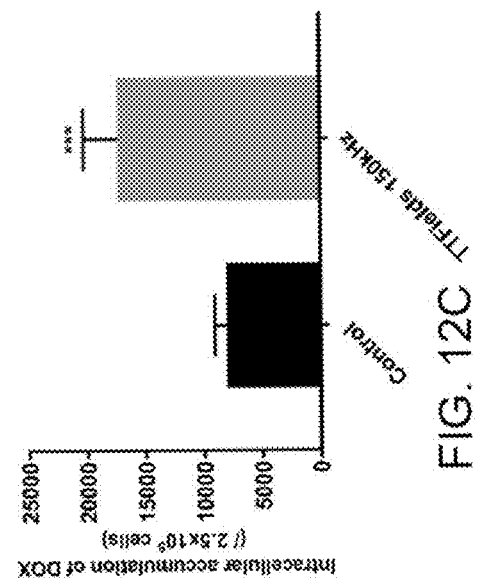
FIG. 12C depicts the results of an experiment to determine how 150 kHz alternating electric fields affect the permeability of the cell membranes of MES-SA cells to doxorubicin.

FIG. 12C depicts the results of another experiment performed to determine how 150 kHz alternating electric fields affect the permeability of the cell membranes of MES-SA cells to doxorubicin (543.52 g/mol). In this experiment, MES-SA cells were treated with an alternating electric field at 150 kHz with a field strength of 1.62 V/cm RMS for 24 hours. After the first 23 hours, doxorubicin at a concentration of 10 μM was added and incubated for one hour during which time the alternating electric fields was continued (to complete the 24 hour period). The intracellular accumulation of doxorubicin was then measured. The intracellular accumulation of doxorubicin increased by more than 2× for the sample that was treated with the 150 kHz alternating electric field.

Figures 13A, 13B:
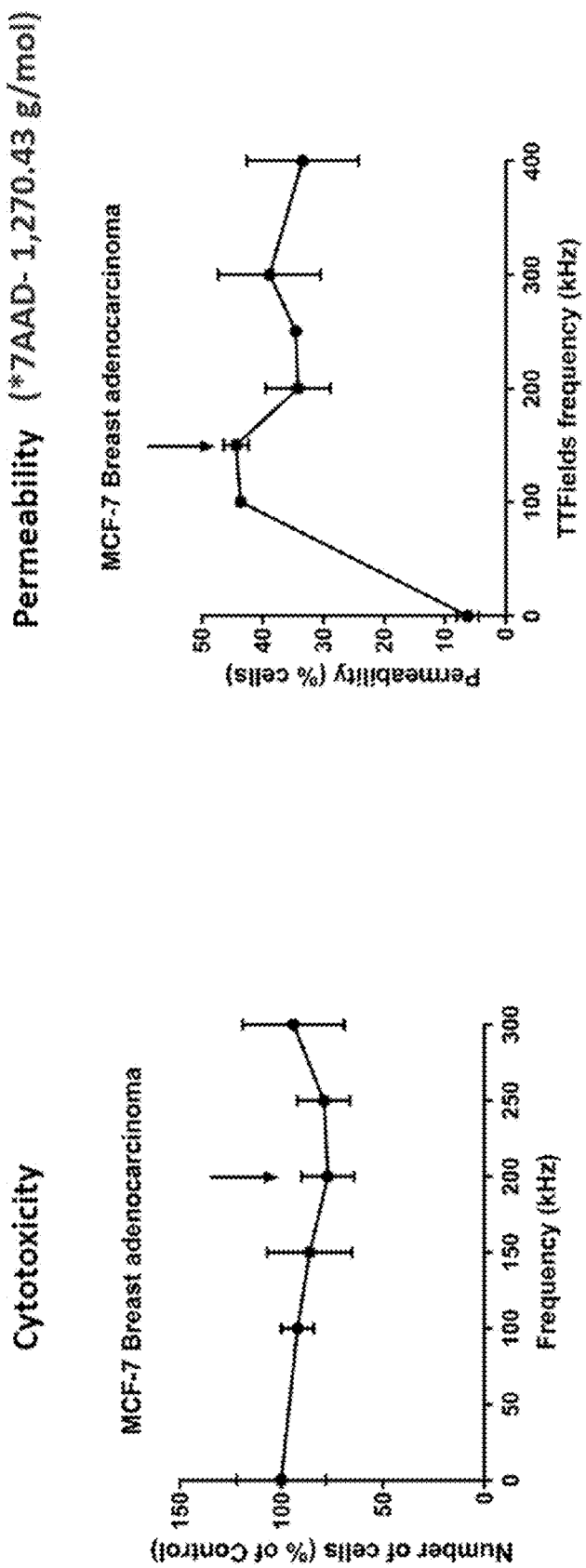
FIG. 13A depicts the results of an experiment to determine the frequency that provides the highest level of cytotoxicity to MCF-7 cells.
FIG. 13B depicts the results of an experiment to determine the frequency that provides the largest increase in permeability of the cell membranes of MCF-7 cells.

FIGS. 13A and 13B depict the results of two in vitro experiments similar to those described above in connection with FIG. 11A/B, except that MCF-7 breast adenocarcinoma cells were used. More specifically, FIG. 13A depicts the results of an experiment to determine the frequency that provides the highest level of cytotoxicity to MCF-7 cells.

The lowest number of MCF-7 cells (which indicates the highest level of cytotoxicity) was observed for the sample that was subjected to alternating electric fields at 200 kHz. FIG. 13B depicts the results of an experiment to determine the frequency that provides the largest increase in permeability of the cell membranes of MCF-7 cells. The highest percentage of MCF-7 cells with increased accumulation of 7-AAD (which indicates the highest level of permeability) was observed for the sample that was subjected to an alternating electric field at 150 kHz.

The experiments described above in connection with FIGS. 11-13 reveal that the optimal frequency for inducing cellular permeability is different from the optimal frequency for inducing cytotoxicity. More specifically, for glioblastoma, the optimal first frequency (for inducing cellular permeability) is between 250 kHz and 350 kHz; and the optimal second frequency (for inducing cytotoxicity) is between 150 kHz and 250 kHz. For uterine sarcoma, the optimal first frequency (for inducing cellular permeability) is between 125 kHz and 175 kHz; and the optimal second frequency (for inducing cytotoxicity) is between 75 kHz and 125 kHz. And for breast adenocarcinoma, the optimal first frequency (for inducing cellular permeability) is between 75 kHz and 175 kHz; and the optimal second frequency (for inducing cytotoxicity) is between 100 kHz and 300 kHz. Pairs of frequency ranges for other types of cancer can be determined experimentally.

When different frequencies are used for inducing cellular permeability and inducing cytotoxicity, the cytotoxicity frequency is preferably applied for the maximum amount of time that can be comfortably tolerated by the patient. Preferably, the cytotoxicity frequency is applied for at least one week. More preferably, the cytotoxicity frequency is applied for many months. Optionally, the interval of time during which the cytotoxicity frequency is applied may be split up into a plurality of non-contiguous intervals of time that are separated by breaks, where the plurality of non-contiguous intervals of time collectively add up to at least one week. In contrast, the frequency for inducing permeability is preferably applied so that the permeability is high when the relevant substance is located in the vicinity of the target cells (e.g., as described above in connection with FIGS. 10A-10B). The application of these two different frequencies may be accomplished using a single AC voltage generator that is controllable to output a first frequency to induce cellular permeability at certain times and a second frequency to induce cytotoxicity at other times. The same set of transducer arrays (i.e., electrodes) may be used to apply the alternating electric fields at these two frequencies (depending on which frequency is applied by the AC voltage generator).

Figure 15:
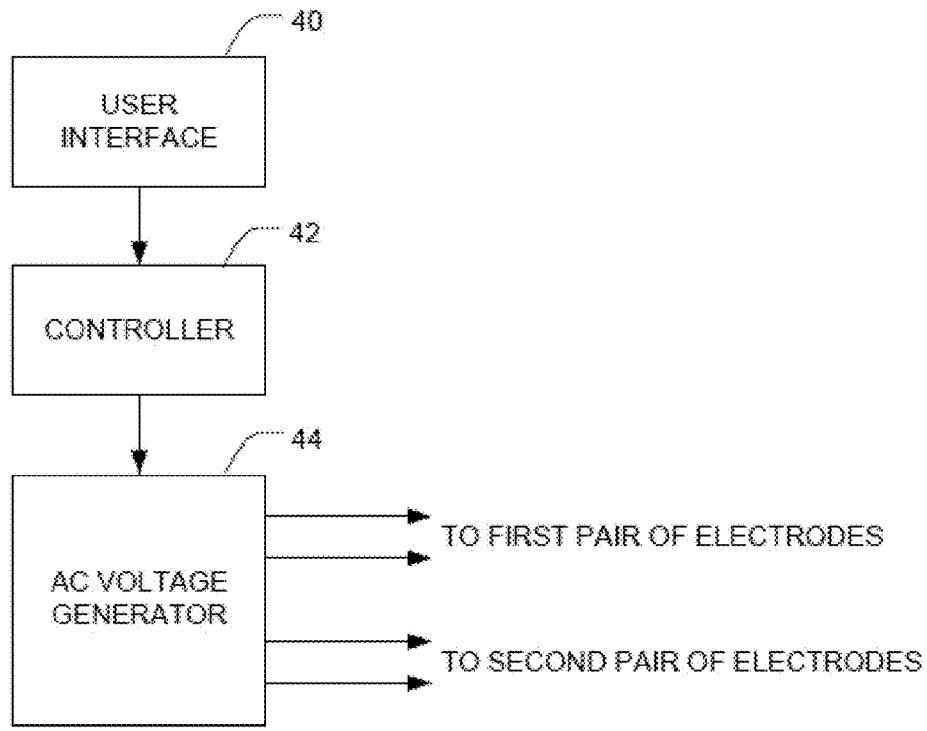
FIG. 15 is a block diagram of a dual-frequency apparatus that generates a first frequency for inducing cellular permeability and a second frequency for inducing cytotoxicity.

FIG. 15 is a block diagram of an apparatus that generates a first frequency for inducing cellular permeability and a second frequency for inducing cytotoxicity. The apparatus includes an AC voltage generator 44 that is similar to the conventional Optune® field generator unit, but has the ability to operate at two different frequencies. Each of those frequencies is between 50 and 500 kHz. This ability may be implemented, for example, using relays to switch either a first set of components or a second set of components into the conventional circuit that generates the AC voltage, and adjusting the operating frequency of an oscillator. The AC voltage generator 44 is configured to output either the first frequency or the second frequency depending on the state of a control input. When the control input is in a first state the AC voltage generator 44 outputs the first frequency, and when the control input is in a second state the AC voltage generator 44 outputs the second frequency. A controller 42 is programmed to place the control input in the second state so that the AC voltage generator 44 outputs the second frequency. The controller 42 is also programmed to accept a request to switch to the first frequency. In the embodiment depicted in FIG. 15, the request arrives via a user interface 40 that may be implemented using any of a variety of conventional approaches including but not limited to a pushbutton, a touch screen, etc. In alternative embodiments, the request may arrive via RF (e.g. Bluetooth, WiFi, etc.) from a tablet, smartphone, etc.

Upon receipt of the request, the controller 42 will place the control input in the first state so that the AC voltage generator 44 will output the first frequency for an interval of time (e.g., at least 1 hour, at least 12 hours, or at least 24 hours). After the interval of time has elapsed, the controller 42 will place the control input in the second state so that the AC voltage generator 44 reverts to outputting the second frequency.

Optionally, the AC voltage generator 44 may be configured to output one or more additional frequencies (e.g., a third frequency, a fourth frequency, etc.), depending on the state of the control input. Preferably each of these additional frequencies is selected to induce cytotoxicity. In these embodiments, the controller 42 is programmed to cycle the control input through the states that cause the AC voltage generator 44 to output the second frequency and the one or more additional frequencies before the request arrives. The controller 42 is also programmed to accept a request to switch to the first frequency. Upon receipt of the request, the controller 42 will place the control input in the first state so that the AC voltage generator 44 will output the first frequency for an interval of time (e.g., at least 1 hour, at least 12 hours, or at least 24 hours). After the interval of time has elapsed, the controller 42 will revert to cycling the control input through the states that cause the AC voltage generator 44 to output the second frequency and the one or more additional frequencies.

The system depicted in FIG. 15 is particularly useful when a person has a tumor that is being treated by combination therapy that includes TTFields and chemotherapy. In this situation, the system operates most of the time at the second frequency to provide the maximum cytotoxicity effect. But when a person visits a chemotherapy clinic for a dose of chemotherapy, healthcare personnel (or the user) actuates the user interface 40 to switch the system to the first frequency that promotes permeability. In this situation, the actuation of the user interface could be done e.g., one hour before the expected start of the chemotherapy, or a short time after the actual start of the chemotherapy.

Alternatively, upon receipt of the request (e.g., from the user interface 40), the controller 42 can control the control input so that the AC voltage generator 44 will output the first frequency for an interval of time (e.g., 1 hour), then switch back and forth between the second frequency and the first frequency (e.g., switching every hour). Eventually (e.g., when the relevant substance has been exhausted from the patient's bloodstream), the controller 42 controls the control input so that the AC voltage generator 44 reverts to outputting the second frequency.

A set of electrodes (not shown) that are similar to the conventional electrodes used with Optune® are connected to the output of the AC voltage generator 44.

Figure 14:
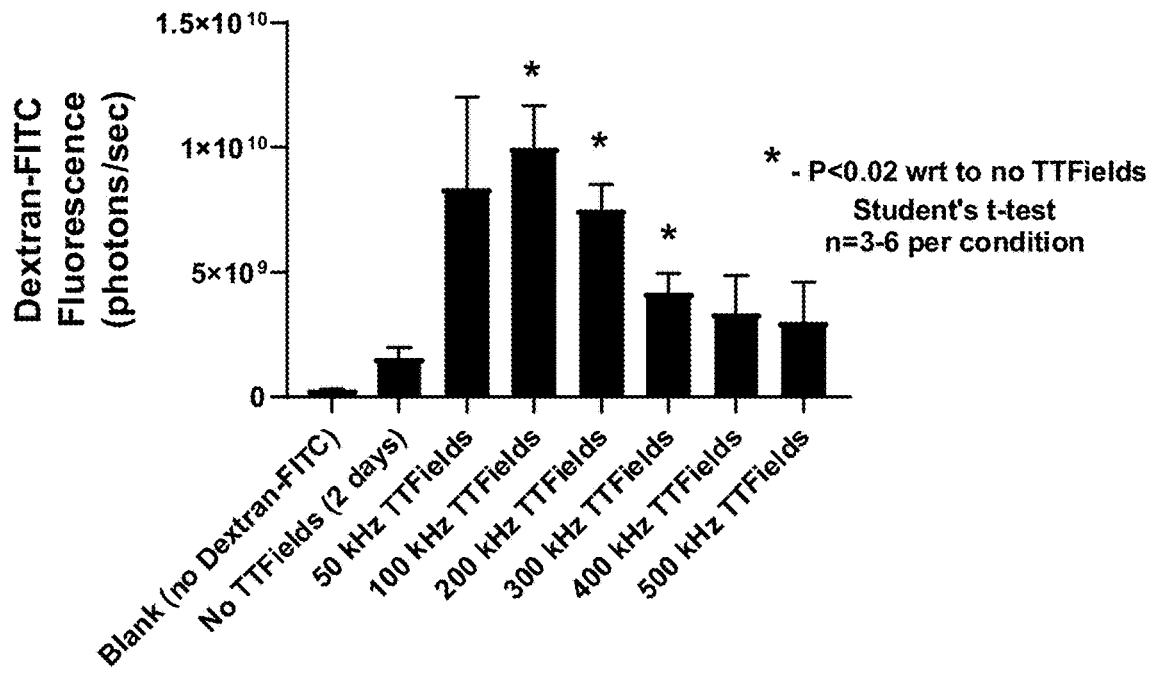
FIG. 14 depicts the results of an experiment to determine the frequency that provides the largest increase in permeability of the cell membranes of GBM39/Luc cells.

FIG. 14 depicts the results of a yet another experiment to determine the frequency that provides the largest increase in permeability of the cell membranes of GBM39/Luc cells. In this experiment, the cells were treated with an alternating electric field at different frequencies in the presence of 4 kDa Dextran FITC (which ordinarily does not readily pass through intact cell membranes) for 2 days. As seen in FIG. 14, the highest level of Dextran-FITC fluorescence (which indicates the highest level of permeability) was observed for the sample that was subjected to an alternating electric field at 100 kHz.

The experimental data discussed in connection with FIGS. 11-14 contain information that is useful for inducing cellular permeability to the maximum extent possible (to enable more of the relevant substance to cross the cell membrane) without regard to any cytotoxicity that may be occurring as a secondary effect. In these situations, the alternating electric field is preferably applied at a single frequency only, selected to induce the highest level of cellular permeability. In some situations (e.g., GBM39/Luc, uterine sarcoma, and breast adenocarcinoma), this frequency will be between 50 and 190 kHz; and in other situations (e.g., U-87 MG glioblastoma), this frequency will be between 210 and 400 kHz.

For those substances that ordinarily can traverse the cell membrane to a significant extent, the techniques described herein for increasing cell membrane permeability can be used to increase the quantity of the substance that will enter the cell. This can improve the therapeutic result provided by those substances. Examples of this class of substances discussed above include ethidium bromide (size=394 Da), doxorubicin (size=544 Da), Mitoxantrone (size=445 Da), etc.

And notably, the techniques described herein can also be used to enable substances that ordinarily could not traverse the cell membrane to a significant extent to enter the cell. Examples of this class of substances discussed above include (a) compounds that are at least 1.2 kDa (e.g., 7-AAD, whose size is 1.27 kDa), (b) compounds that are at least 4 kDa (e.g., 4 kDa Dextran-FITC, and (c) compounds that are at least 20 kDa (e.g., 20 kDa Dextran-FITC), (d) genetic material including but not restricted to supercoiled plasmid DNA, siRNA, and shRNA constructs, (e) genome editing system including but not restricted to meganucleases, zinc finger nucleases (ZFNs), transcription activator-like effector-based nucleases (TALEN) and clustered regularly interspaced short palindromic repeats (CRISPR/Cas9), (f) any form of an antibody including but not limited to IgG, Fab, Fab', F(ab')2, scFv, di-scFv, sdAb. Such antibody can be either unconjugated or conjugated to cytotoxic agent, toxin, fluorophore, quantum dots, and enzymes, (g) charged molecules, and (h) small molecules, therapeutic entities, peptides, and proteins that typically do not permeate the cell membrane or are being destroyed during endocytosis. Providing the ability to get these substances through the cell membrane means that compounds that may previously have been rejected as ineffective in a compound-screening process (due to their inability to traverse the cell membrane) may suddenly become usable for therapeutic purposes when used in combination with an alternating electric field that enhances cellular permeability.

The methods described herein may also be useful beyond the context of cancer cells. More specifically, the methods described herein may be useful to deliver large molecules (which ordinarily would not pass through the relevant cell membrane) through a cell membrane of certain other non-cancerous cells (e.g., kidney cells, lung cells, liver cells, heart cells, brain cells, muscle cells, bone marrow cells, etc.). Delivery of such drugs can be enhanced by applying alternating electric fields to the relevant body part for a period of time (e.g., 24 hours) prior to and during administration those drugs. Candidates for such drugs include but are not limited to antiepileptic drugs and psychotropic drugs (e.g., olanzapine, 9-OH risperidone and other varieties of risperidone, etc.).

In yet another example, it may be possible to achieve localized enhancement of drug uptake in bacteria by applying alternating electric fields to the relevant body part for a period of time (e.g., 24 hours) prior to and during administration of a suitable antibiotic. In situations where a particular bacteria has evolved to be drug resistant or multidrug-resistant (e.g., based on a mechanism of action that involves the cell membrane), the application of alternating electric fields may increase the permeability of the bacteria's cell membrane to the point where the resistance can be overcome. Similar approaches may be used to enhance drug uptake to combat meningitis, pneumonia, infective endocarditis, etc. Note that in the in vivo context, the alternating electric fields may be applied to a target region (e.g., the lungs) that is tumor free. Alternatively, the alternating electric fields may be applied it to a target region that contains a tumor (e.g., a brain that includes a glioblastoma).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the claims listed below, and equivalents thereof Material and Methods Cell Culture Studies:

Two patient-derived GBM lines (GBM2, GBM39), a commercially available human GBM cell line (U87-MG from ATCC, Manassas, Va., USA) as well as a murine astrocytoma cell line, (KR158B; a gift from Dr. Duane Mitchell of the Department of Neurosurgery at the University of Florida School of Medicine) were used. Human U87-MG, human PCS-201 and murine KR158B glioblastoma cell lines were grown in DMEM (Invitrogen/Life Technologies, Carlsbad, Calif., USA)/10% FBS/and 1× antibiotic-antimycotic (Invitrogen/Life Technologies, Carlsbad, Calif.). GBM2 and GBM39 were grown in a defined, serum-free media whose composition has been described previously.

Seeding of Cells onto Glass Coverslips for TTFields Experiments:

Briefly, cells in culture were trypsinized via standard protocols and 10,000-50,000 single cells were suspended in 200 or 75 µL of DMEM/10% FBS/1×antibiotic-antimycotic and then were seeded onto the center of a 22 mm or 12 mm diameter glass Thermanox™ coverslips respectively (ThermoFisher Scientific, Waltham, Mass., USA). The cells were incubated overnight in a humidified 95% air/5% $CO_2$ incubator set at 37° C. Once the cells became attached to the coverslip, 2 mL or 1 mL of DMEM/10% FBS/lx antibiotic-antimycotic was added per well of 6-well or 12-well plates, respectively. Unless otherwise stated in the Results section, the cells were left to grow on the coverslip for two to three days (in order to ensure cells were in the growth phase) before being transferred to ceramic dishes of an Inovitro™ in vitro TTFields apparatus (Novocure Inc., Haifa, Israel). Growth conditions (i.e., time cells allowed to grow under TTFields-exposed vs. unexposed conditions) are specified either in the Results section or in the corresponding figure legends.

In Vitro Tumor Treating Field Apparatus:

The coverslips were transferred to a ceramic dish of the Inovitro™ system, which in turn was mounted onto Inovitro™ base plates (Novocure Ltd., Haifa, Israel). Tumor treating fields at 200 kHz (1-4 V/cm) were applied through an Inovitro™ power generator. Incubator ambient temperatures spanned 20-27° C. with a target temperature of 37° C. in the ceramic dishes upon application of the TTFields. Duration of TTFields exposure lasted anywhere from 0.5 to 72 h, after which coverslips were removed and processed for the appropriate bioassays (see below). For reversibility experiments, the TTFields-exposed coverslips were transferred to a regular incubator without TTFields exposure for 24 h (off TTFields period to assess for reversibility of the TTFields effect on cell membrane permeability) prior to processing for the appropriate bioassays. Culture media were exchanged manually every 24 h throughout the experiments to account for evaporation. Corresponding control experiments (no TTFields) were done by placing equivalent coverslips within 6-well or 12-well plates into a conventional humidified tissue culture incubator (37° C., 95% air/5% $CO_2$) and cells grown in parallel with the TTFields-exposed coverslips. Unless otherwise mentioned, all experiments were done in at least triplicate samples per condition and per time point.

Cell Counting Assay Via Hemocytometer:

Preparation of cells for counting was achieved via established protocols and visualized on a Zeiss PrimoVert benchtop microscope (Dublin, Calif., USA). Unless otherwise stated, cell counts were done on trypsinized, single-cell suspensions with a hemocytometer and the mean of the four cell-count measurements was calculated and rounded to the nearest integer.

Bioluminescence Imaging:

For all bioluminescence work, we used genetically-modified GBM2, GBM39 and U87-MG whereby the glioblastoma cells were transfected with lentiviral vectors that expressed either firefly luciferase (fLuc for GBM39) or a fusion protein of GFP and firefly luciferase (GFP/fLuc for GBM2 and eGFP-fLuc for U87-MG) or a Renilla luciferase-Red Fluorescence protein fusion (RLuc-RL8 for KR158B). Cells were transduced using viral supernatants, and expression of luciferases was confirmed by measuring cellular luciferase activity (IVIS Spectrum; Perkin Elmer, Waltham, Mass.) in the presence of D-Luciferin (0.3 mg/mL final concentration) for fLuc and coelenterazine (1 µg/mL) for rLuc.

Scanning Electron Microscopy (SEM):

5,000 (low seeding condition) to 50,000 (high seeding condition) U87-MG/eGFP-fLuc cells or PCS-201 fibroblast cells were deposited onto 13 mm glass coverslips and then prepared for TTFields experiments. Cells were grown under standard tissue culture incubator conditions (37° C., 95% O2, 5% $CO_2$). At the end of the TTFields-exposed and TTFields-unexposed experiments (1 day for high-seeding conditions and 3 days for low-seeding conditions), the coverslips were processed for SEM. All ROI analyses were performed in a blinded manner in which neither the individual responsible for SEM image acquisition nor the one performing data analyses knew of the experimental conditions for the samples. A third individual had possession of the sample identities.

Chemical Reagents:

Unless otherwise stated, all chemicals were purchased from Selleckchem Inc. (Houston, Tex., USA), Thermo-Fisher Scientific (Waltham, Mass., USA), or Sigma-Aldrich (St. Louis, Mo., USA). Purified firefly luciferin or firefly luciferase (SRE0045-2 MG) as well as the Ethidium D apoptosis kit (11835246001) were purchased from Sigma Aldrich Inc (St. Louis, Mo.). Dextran-FITC of molecular weights 4, 20, and 50 kDa (FD4, FD20 and FD50), were purchased from Sigma Aldrich Inc. as well. 5-aminolevulinic acid (5-ALA, AAA16942ME) and the AnnexinV-APC kit (50712549) were purchased from Thermo-Fisher Scientific Inc (Waltham, Mass.).

Statistical Analysis:

The PRISM 7.0 software (GraphPad Software Inc., La Jolla, Calif., USA) was used to determine whether the data were normally distributed. Normally distributed data were analyzed with two-way Student's t-test or analysis of variance (ANOVA) comparisons of means, while nonnormally-distributed data were analyzed with nonparametric analyses (e.g., Mann-Whitney U test comparison of medians). The level of statistical significance was set at alpha=0.05. Bonferroni or Dunnet post-hoc corrections were employed to adjust alpha for multiple comparisons. All data are presented as range, mean±standard deviation, median (interquartile range), or percent. In all figures, the levels of statistically significant differences are represented by: *$p<0.05$, $p<0.01$, and *$p<0.001$.

What is claimed is:

1. An apparatus for treating a tumor in a subject's body and facilitating delivery of a substance across cell membranes in the subject's body, the apparatus comprising:

an AC voltage generator capable of operating at a first frequency between 50 and 500 kHz and a second frequency between 50 and 500 kHz, wherein the second frequency is different from the first frequency, the AC voltage generator having a control input, wherein the AC voltage generator is configured to output the first frequency when the control input is in a first state and to output the second frequency when the control input is in a second state; and a controller programmed to (a) place the control input in the second state so that the AC voltage generator outputs the second frequency, (b) accept a request to switch to the first frequency, (c) upon receipt of the request, place the control input in the first state so that the AC voltage generator outputs the first frequency for an interval of time, and (d) when the interval of time has elapsed, automatically place the control input in the second state so that the AC voltage generator outputs the second frequency, wherein the first frequency is selected to increase permeability of the cell membranes and the second frequency is selected to reduce viability of the cells in the tumor, and wherein the interval of time is at least 12 hours.

2. The apparatus of claim 1, further comprising:

a set of electrodes configured for affixation to the subject's body; and wiring that connects an output of the AC voltage generator to the set of electrodes.

3. The apparatus of claim 1, wherein the first frequency is between 250 kHz and 350 kHz, and the second frequency is between 150 kHz and 250 kHz.

4. The apparatus of claim 1, wherein the first frequency is between 125 kHz and 175 kHz, and the second frequency is between 75 kHz and 125 kHz.

5. The apparatus of claim 1, wherein the first frequency is between 75 kHz and 175 kHz, and the second frequency is between 100 kHz and 300 kHz.

6. The apparatus of claim 1, wherein the controller is further programmed to, subsequent to the receipt of the request, switch the control input back and forth between the first state and the second state.

7. The apparatus of claim 1, wherein the AC voltage generator is capable of operating at at least one additional frequency between 50 and 500 kHz, and wherein the AC voltage generator is configured to output the least one additional frequency when the control input is in at least one additional state, and
wherein the controller is programmed to cycle the control input through the second state and the at least one additional state prior to receipt of the request, and to cycle the control input through the second state and the at least one additional state after the interval of time has elapsed.

8. The apparatus of claim 1, further comprising a user interface, wherein the request is accepted via the user interface.

9. An apparatus for treating a tumor in a subject's body and facilitating delivery of a substance across cell membranes in the subject's body, the apparatus comprising:
an AC voltage generator capable of operating at a first frequency between 50 and 500 kHz and a second frequency between 50 and 500 kHz, wherein the second frequency is different from the first frequency, the AC voltage generator having a control input, wherein the AC voltage generator is configured to output the first frequency when the control input is in a first state and to output the second frequency when the control input is in a second state; and
a controller programmed to (a) place the control input in the second state so that the AC voltage generator outputs the second frequency, (b) accept a request to switch to the first frequency, (c) upon receipt of the request, place the control input in the first state so that the AC voltage generator outputs the first frequency for an interval of time, and (d) when the interval of time has elapsed, automatically place the control input in the second state so that the AC voltage generator outputs the second frequency,
wherein the first frequency is selected to increase permeability of the cell membranes and the second frequency is selected to reduce viability of the cells in the tumor, and
wherein the interval of time is between 12 and 72 hours.

10. The apparatus of claim 9, further comprising:
a set of electrodes configured for affixation to the subject's body; and
wiring that connects an output of the AC voltage generator to the set of electrodes.

11. The apparatus of claim 9, wherein the first frequency is between 250 kHz and 350 kHz, and the second frequency is between 150 kHz and 250 kHz.

12. The apparatus of claim 9, wherein the first frequency is between 125 kHz and 175 kHz, and the second frequency is between 75 kHz and 125 kHz.

13. The apparatus of claim 9, wherein the first frequency is between 75 kHz and 175 kHz, and the second frequency is between 100 kHz and 300 kHz.

14. The apparatus of claim 9, wherein the controller is further programmed to, subsequent to the receipt of the request, switch the control input back and forth between the first state and the second state.

15. The apparatus of claim 9, wherein the AC voltage generator is capable of operating at at least one additional frequency between 50 and 500 kHz, and wherein the AC voltage generator is configured to output the least one additional frequency when the control input is in at least one additional state, and
wherein the controller is programmed to cycle the control input through the second state and the at least one additional state prior to receipt of the request, and to cycle the control input through the second state and the at least one additional state after the interval of time has elapsed.

16. A method for treating a tumor in a subject's body and facilitating delivery of a substance across cell membranes in the subject's body, the method comprising:
applying an electric field at a second frequency between 50 and 500 kHz to the tumor, wherein the second frequency is selected to reduce viability of the cells in the tumor;
accepting a request to switch to a first frequency;
upon receipt of the request, applying an electric field at the first frequency between 50 and 500 kHz to the tumor for an interval of time, wherein the first frequency is selected to increase permeability of the cell membranes and wherein the second frequency is different from the first frequency; and
automatically reverting to applying the electric field at the second frequency to the tumor when the interval of time has elapsed,
wherein the interval of time is at least 12 hours.

17. The method of claim 16, wherein the first frequency is between 250 kHz and 350 kHz, and the second frequency is between 150 kHz and 250 kHz.

18. The method of claim 16, wherein the first frequency is between 125 kHz and 175 kHz, and the second frequency is between 75 kHz and 125 kHz.

19. The method of claim 16, wherein the first frequency is between 75 kHz and 175 kHz, and the second frequency is between 100 kHz and 300 kHz.

20. The method of claim 16, wherein the interval of time is between 12 and 72 hours.

* * * * *